US006809225B2

(12) United States Patent
Donsbach et al.

(10) Patent No.: US 6,809,225 B2
(45) Date of Patent: Oct. 26, 2004

(54) METHOD FOR PRODUCING 3,3-DIARYLPROPYLAMINES

(75) Inventors: Martin Donsbach, Monheim (DE); Peter Eilbracht, Dortmund (DE); Christian Buss, Dortmund (DE); Andreas Schmidt, Dortmund (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 10/332,290
(22) PCT Filed: Jul. 6, 2001
(86) PCT No.: PCT/EP01/07803

§ 371 (c)(1),
(2), (4) Date: Jul. 14, 2003

(87) PCT Pub. No.: WO02/04399

PCT Pub. Date: Jan. 17, 2002

(65) Prior Publication Data
US 2004/0034080 A1 Feb. 19, 2004

(30) Foreign Application Priority Data

Jul. 7, 2000 (DE) .......................................... 100 33 016

(51) Int. Cl.$^7$ .............................................. C07C 205/04
(52) U.S. Cl. ........................................ 568/707; 568/708
(58) Field of Search ................................. 568/707, 708

(56) References Cited

FOREIGN PATENT DOCUMENTS

| WO | WO 94/11337 | 5/1994 |
| WO | WO 97/44329 | 11/1997 |
| WO | WO 98/29402 | 7/1998 |
| WO | WO 99/58478 | 11/1999 |

OTHER PUBLICATIONS

*Modern Synthetic Methods* (1989), Biotransformations in Organic Synthesis, Enantioselective Catalysis with Metal Complexes, Aluminosilicates in Organic Synthesis, pp. 158–165, 178–179 and 194–195.

*Primary Examiner*—Taofiq Solola
(74) *Attorney, Agent, or Firm*—Peter F. Corless; John B. Alexander; Edwards & Angell, LLP

(57) ABSTRACT

A novel method is described for producing 3,3-diarylpropylamines by hyroformylation/hydrocarbonylation and then reductive amination using a transition metal catalyst.

21 Claims, No Drawings

METHOD FOR PRODUCING 3,3-DIARYLPROPYLAMINES

The invention relates to a novel method for producing substituted 3,3-diarylpropylamine derivatives. In particular, it relates to the production of such compounds by hydrocarbonylation/hydroformylation with subsequent reductive amination.

The abovementioned 3,3-diarylpropylamine derivatives are used in the treatment of urinary incontinence and other spasmogenic conditions (see WO 99/58478). The methods described there for producing the 3,3-diphenylpropylamine derivatives are for the most part multi-stage and for the production of optically active compounds require for the most part enantiomer separation.

The underlying object of the invention is, therefore, to provide new methods for the production of substituted 3,3-diarylpropylamine derivatives, that are simpler than the ones described in the state of the art, i.e. involve less stages, and that, apart from this, allow a stereo-selective synthesis of the target compounds.

The object of the invention is a method for producing 3,3-diarylpropylamines of the general formula I

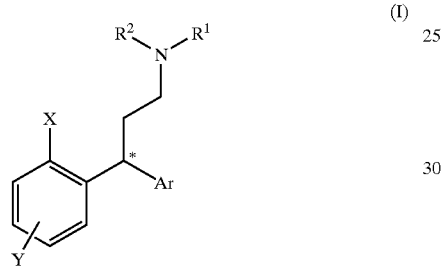

wherein
Ar represents a substituted or unsubstituted aryl radical,
X represents H, OH or $OR^3$,
Y represents Cl, Br, I, CN, CHO, $CH_2OR$, COOH, COOR, wherein R represents $C_1-C_{10}$-alkyl or a substituted or unsubstituted aryl radical, or $C_1-C_{10}$-alkyl,
$R^1$, $R^2$ represents $C_1-C_{10}$-alkyl or $C_3-C_8$-cycloalkyl, wherein $R^1$ and $R^2$ can be linked to form a cyclical structure,
and wherein $R^3$ represents a radical, that is derived from one of the following compounds:
(i) the amino acids D-proline, L-proline, D-alanine, L-alanine, D-asparagine, L-asparagine, D-asparagine acid, L-asparagine acid, D-glutamine, L-glutamine, D-glutamine acid, L-glutamine acid, D-phenylalanine, L-phenylalanine, D-histidine, L-histidine, D-leucine, L-leucine, D-serine, L-serine, L-threonine, D-threonine, D-tryptophane, L-tryptophane, D-tyrosine, L-tyrosine, D-valine, L-valine, D-cysteine, L-cysteine, D-methionine, L-methionine, D-isoleucine, L-isoleucine, or the alcohols that are produced by these amino acids by reduction of the carboxylic acid function to the hydroxymethylene unit,
(ii) the amino acids N-diphenylphosphanyl-D-alanine, N-diphenylphosphanyl-L-alanine, N-diphenylphosphanyl-D-proline, N-diphenylphosphanyl-L-proline, N-diphenylphosphanyl-D-phenylalanine, N-diphenylphosphanyl-L-phenylalanine, and the alcohols that are produced by these amino acids by reduction of the carboxylic acid function to the hydroxymethylene unit, (iii) α-hydroxycarboxylic acid derivatives of the general formula

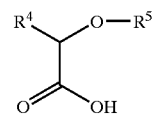

respectively in the form of both optical antipodes, wherein $R^4$ represents a linear or branched $C_1-C_{10}$-alkyl group or cycloalkyl group or a substituted or unsubstituted aryl radical and $R^5$ represents $C_1-C_{10}$-alkyl, cycloalkyl, acyl, alkoxycarbonyl, benzoyl, diphenylphosphanyl, dicyclohexylphosphanyl or diarylphosphanyl, (iv) the compounds of the general formula

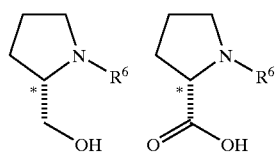

wherein $R^6$ represents a substituent selected from the group comprising $PPh_2$, $P(C_6H_{11})_2$, $P(aryl)_2$, alkyl, acyl, alkoxycarbonyl, benzoyl, arylcarbonyl, diarylphosphanyl and dicyclohexylphosphanyl, and their stereoisomers, (v) the compounds of the general formula

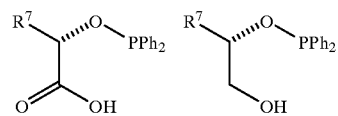

wherein $R^7$ represents a linear or branched $C_1-C_{10}$-alkyl group or a substituted or unsubstituted aryl radical, and stereoisomers of this, (vi) the acids (R)-acetoxyphenylacetic acid, (R)- and (S)-1,4-benzodioxane-2-carboxylic acid, (R)-(−)- and (S)-(+)-hexahydro-acetoxymandelic acid, (2R, 3S)-2,3-O-isopropylidene-2,3-dihydroxybutyric acid and its stereoisomers, (+)- and (−)-menthyloxyacetic acid, (R)- and (S)-3-phenyl-2-acyloxypropionic acid, (R)- and (S)-acetoxymandelic acid, (R)- and (S)-α-methoxy-α-trifluoromethylphenylacetic acid, (S)-(+)-alpha-methoxyphenylacetic acid, (R)- and (S)-5-oxo-tetrahydrofurane-2-carboxylic acid, and the alcohols that are produced from these acids by reduction of the carboxylic acid function to the hydroxymethylene unit, (vii) compounds of the general formula

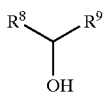

wherein $R^8$ represents a substituted or unsubstituted aryl radical and $R^9$ a hydrogen or a linear or branched $C_1$–$C_{10}$-alkyl radical, (viii) α-naphthol, β-naphthol or (R)- or (S)-1-(9-anthryl)-2,2,2-trifluoroethanol, (ix) 2-methylamino-1-phenyl-propan-1-ol (ephedrine) in all stereomer forms, or $R^3$ represents one of the following radicals:

(x) phosphite radicals of the general formula —P(OR$^{10}$)(OR$^{11}$), wherein $R^{10}$ and $R^{11}$ can be the same or different and represent an if necessary polycyclic or bridged aryl radical, (xi) $C_1$–$C_{10}$-alkyl, branched or linear, (xii) acyl, (xiii) benzyl or substituted benzyl radicals, characterised in that compounds of the general formula (II)

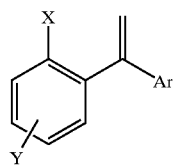

(II)

wherein X, Y and Ar are as defined above, are transformed together with carbon monoxide (CO) and hydrogen ($H_2$) in the presence of a transition metal catalyst and the resultant oxo compounds are allowed to react in the presence of a transition metal catalyst with an amine of the general formula HNR$^1$R$^2$, wherein $R^1$ and $R^2$ are as defined above.

In formula I, the substituent X represents hydrogen (H), hydroxy (OH) or the group OR$^3$.

Here, the substituent $R^3$ can have the meaning assigned to substituents R and R' in claim 1 of patent WO 99/58478.

$R^3$ preferably represents a radical that is derived from the following compounds and alcohols:

(i) the amino acids D-proline, L-proline, D-alanine, L-alanine, D-asparagine, L-asparagine, D-asparagine acid, L-asparagine acid, D-glutamine, L-glutamine, D-glutamine acid, L-glutamine acid, D-phenylalanine, L-phenylalanine, D-histidine, L-histidine, D-leucine, L-leucine, D-serine, L-serine, D-threonine, L-threonine, D-tryptophane, L-tryptophane, D-tyrosine, L-tyrosine, D-valine, L-valine, D-cysteine, L-cysteine, D-methionine, L-methionine, D-isoleucine, L-isoleucine, or the alcohols that are produced by these amino acids by reduction of the carboxylic acid function to the hydroxymethylene unit.

In these amino acid radicals, the bonding to the oxygen atom takes place according to the formula —O—$R^3$ via the OH group of the abovementioned amino acids, as shown in the following graphic formula:

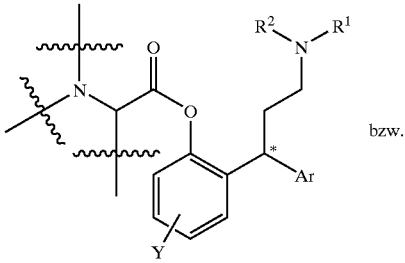

bzw.

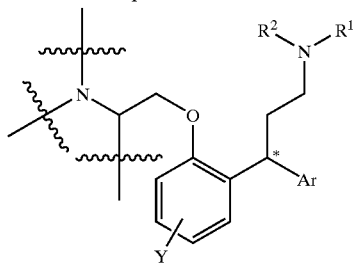

bzw. = or (ii) Furthermore, the substituent $R^3$ can be derived from the following amino acid derivatives:
the amino acids N-diphenylphosphanyl-D-alanine, N-diphenylphosphanyl-L-alanine, N-diphenylphosphanyl-D-proline, N-diphenylphosphanyl-L-proline, N-diphenylphosphanyl-D-phenylalanine, N-diphenylphosphanyl-L-phenylalanine, and the alcohols that are produced by these amino acids by reduction of the carboxylic acid function to the hydroxymethylene unit.

(iii) According to a further embodiment $R^3$ can be derived from the following α-hydroxycarboxylic acids:
α-hydroxycarboxylic acid derivatives of the general formula

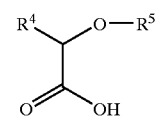

respectively in the form of both optical antipodes, wherein $R^4$ represents a linear or branched $C_1$–$C_{10}$-alkyl group or cycloalkyl group or a substituted or unsubstituted aryl radical and $R^5$ represents $C_1$–$C_{10}$-alkyl, cycloalkyl, acyl, alkoxycarbonyl, benzoyl, diphenylphosphanyl, dicyclohexylphosphanyl or diarylphosphanyl.

Preferred examples are (R)- and (S)-acetoxy-phenylacetic acid, (S)-(+)- and R-(−)-alphamethoxyphenylacetic acid, (R)- and (S)-3-phenyl-2-acyloxypropionic acid.

(iv) $R^3$ can, furthermore, be derived from the carboxylic acids or alcohols shown below:

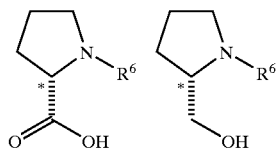

wherein $R^6$ represents a substituent selected from the group comprising PPh$_2$, alkyl, acyl, alkoxycarbonyl, benzoyl, arylcarbonyl, diphenylphosphanyl, diarylphosphanyl and dicyclohexylphosphanyl, and stereoisomers of these.

(v) Furthermore, $R^3$ be derived from the carboxylic acids or alcohols shown below:

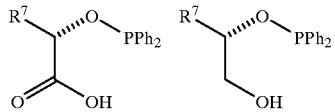

wherein $R^7$ represents a linear or branched $C_1$–$C_{10}$-alkyl group or a substituted or unsubstituted aryl radical, and stereoisomers of this.

(vi) Furthermore, the substituent $R^3$ can be derived from one of the carboxylic acids shown below:

1. (R)-acetoxyphenylacetic acid or the enantiomer

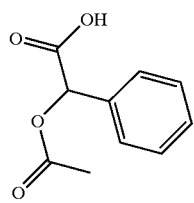

2. (R)-1,4-benzodioxane-2-carboxylic acid or the enantiomer

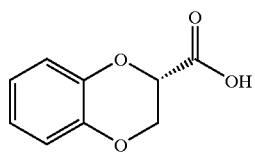

3. (R)-(−)-hexahydroacetoxymandelic acid or the enantiomer

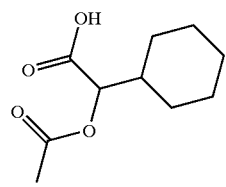

4. (2R, 3S)-2,3-O-isopropylidene-2,3-dihydroxy-butyric acid or the enantiomer

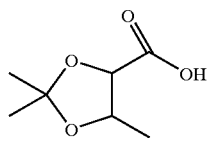

5. (+)-menthyloxyacetic acid or the enantiomer

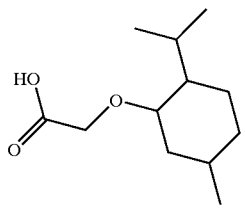

6. (S)-(+)-alpha-menthoxyphenylacetic acid or the enantiomer

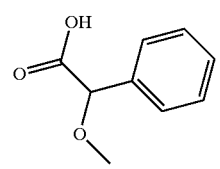

7. (R)-5-oxo-tetrahydrofurane-2-carboxylic acid or the enantiomer

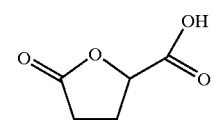

8. (R)-3-phenyl-2-acyloxypropionic acid or the enantiomer

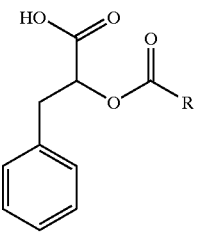

wherein R is as defined above.

9. (R)-α-methoxy-α-trifluoromethylphenylacetic acid or the enantiomer

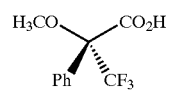

All the abovementioned acids have one or more asymmetric centres and are used in an optically active manner. The bonding of the acids to the oxygen atom according to the formula —O—$R^3$ again takes place as in the other abovementioned carboxylic acids or alcohols via the OH group, so that generally esters or ethers with the following structure result:

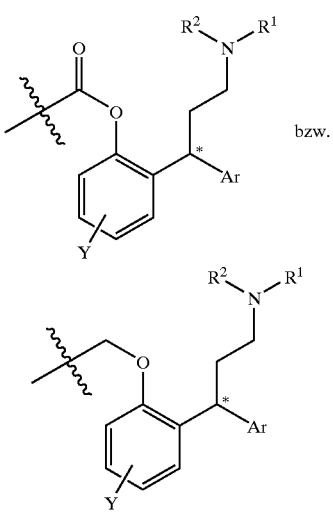

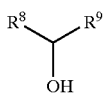

bzw. = or (vii) The radical $R^3$ can, furthermore, be derived from compounds of the general formula $$R^8 \quad R^9$$
$$OH$$

wherein $R^8$ represents a substituted or unsubstituted aryl radical and $R^9$ hydrogen or a linear or branched $C_1$–$C_{10}$-alkyl radical.

Again, the bonding of the substituted $R^3$ takes place via the oxygen atom, so that aryl ethers result.

(viii) The substituent $R^3$ can, furthermore, be derived from α-naphthol, β-naphthol or (R)- or (S)-1-(9-anthryl)-2,2,2-trifluorethanol.

Here also the bonding takes place via the oxygen atom.

(ix) According to a further embodiment, $R^3$ can be derived from ephedrine, i.e. 2-methylamino-1-phenylpropan-1-ol. This compound is chiral and within the context of the present invention all stereoisomer forms must be included with this.

The bonding of $R^3$ again takes place via the oxygen atom, so that an ether structure results.

(x) Finally, $R^3$ can also represent a phosphite radical of the general formula —P(OR$^{10}$) (OR$^{11}$), wherein $R^{10}$ and $R^{11}$ can be the same or different and represent an if necessary polycyclic or bridged aryl radical.

Preferred examples are phosphate radicals with the formulas

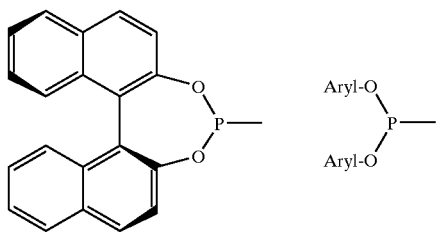

Furthermore, $R^3$ can represent:
(xi) $C_1$–$C_{10}$-alkyl, linear or branched,
(xii) acyl,
(xiii) benzyl or substituted benzyl radicals.

The substituent Y according to the general formula I represents Cl, Br, I, CN, COOH, COOR, CHO, CH$_2$OR or $C_1$–$C_{10}$-alkyl.

In the group COOR or CH$_2$OR the substituent R represents a linear or branched $C_1$–$C_{10}$-alkyl group or a substituted or unsubstituted aryl radical.

The substituent Y is selected so that it can be converted using simple, generally-known methods into a hydroxymethyl group. By way of example, an ester or carboxylic acid group is reduced directly, a halide can be converted via a Grignard intermediate stage into the corresponding carboxylic acid and then reduced, and a nitrile can first, for example, be hydrolysed to form the carboxylic acid and then reduced to a hydroxymethyl group.

Through this conversion of the substituent Y into a hydroxymethyl group, the 3,3-diphenylpropylamine derivatives described in WO 99/58478 can be produced in a simpler way. Suitable methods for converting the substituent Y into a hydroxymethyl group are also described there.

According to a preferred embodiment of the method according to the invention Y represents an ester group that is at paraposition to the substituent X.

Finally, the substituents $R^1$ and $R^2$, that can be the same or different, represent a $C_1$–$C_{10}$-alkyl group or a $C_3$–$C_8$-cycloalkyl group, wherein $R^1$ and $R^2$ can be linked to form a cyclical structure. This cyclical structure can contain heteroatoms, such as nitrogen, oxygen, etc., so that $R^1$ and $R^2$ together with the nitrogen atom, to which they are bonded, can, for example, form a morpholine radical.

According to a preferred embodiment of the method according to the invention, $R^1$ and $R^2$ represent isopropyl and AR represents phenyl.

Within the context of the present invention, the term "alkyl" means a linear or branched hydrocarbon chain with preferably between 1 and 10 C-atoms. Examples of such alkyl groups include methyl, ethyl, propyl, isopropyl, butyl, isobutyl, t-Butyl and suitable isomers of pentyl and hexyl, wherein the isopropyl group is preferred.

The term "cycloalkyl" or "cycloalkyl group" describes cyclical hydrocarbon radicals with preferably between 3 and 10 carbon atoms, which can be substituted if necessary.

In the context of the present invention, substituents means groups known to a person skilled in the art such as alkyl, alkoxy, halogen (fluorine, chlorine, bromine, iodine), nitro and similar groups.

The term "substituted or unsubstituted benzyl" describes a benzyl group whose phenyl ring is substituted if necessary one or more times. Substituted benzyl groups are preferably 4-methylbenzyl, 4-methoxybenzyl, 4-nitrobenzyl, 2-nitrobenzyl, 4-chlorobenzyl and 2-chlorobenzyl.

The term "alkylcarbonyl" describes groups of the formula R—C(=O), wherein R represents an alkyl group. Preferred alkyl carbonyl groups are acetyl, proprionyl, isobutyryl, valeroyl and pivaloyl.

The term "cycloalkylcarbonyl" describes a group of the formula R—C(=O), wherein R represents a cycloalkyl group.

The term "aryl" designates an aromatic hydrocarbon radical such as phenyl ($C_6H_5$—), naphthyl ($C_{10}H_7$—) and anthryl ($C_{14}H_9$—). Phenyl and naphthyl groups are preferred, in particular phenyl groups, wherein these groups can be substituted one or more times. If necessary, two or more aryl radicals can be bridged or condensed with each other to form polycyclic structures.

The term "benzoyl" describes acyl groups of the formula —C(=O)—Ph, wherein the phenyl ring again can be substituted one or more times. Examples of such substituted acyl groups include 4-methoxybenzoyl, 2-methoxybenzoyl, 4-chlorobenzoyl, 2-chlorobenzoyl, 4-nitrobenzoyl and 2-nitrobenzoyl.

The term "alkoxycarbonyl" stands for R—OC (=O) groups, wherein R represents an alkyl group. Preferred alkoxycarbonyl groups are methoxycarbonyl, ethoxycarbonyl, propoxycarbonyl, t-butyloxycarbonyl and benzyloxycarbonyl as well as alicyclic alkoxycarbonyl groups.

The term "amino acid" or "amino acid radical" describes radicals that are derived from naturally occurring or synthetic amino acids (including all optical antipodes). Preferred amino acid radicals are valyl, leucyl, isoleucyl, phenylalanyl, prolyl, seryl, threonyl, methionyl and hydroxyprolyl.

The amino acid radical can be substituted by a suitable group. Examples of such substituted amino acid radicals are N-benzoylprolyl, N-tert.-butoxycarbonylprolyl, N-alkyl, N-acyl or N-diphenylphosphanylprolyl.

The method according to the invention is based on the hydrocarbonylation/hydroformylation of compounds of the general formula

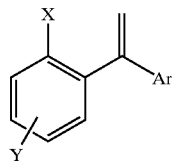

wherein X, Y and Ar are as defined above, and a subsequent reductive amination of the corresponding oxo-compounds. The oxo-compounds can be isolated or also converted in a "one-step" reaction directly to the corresponding diarylamines. The method according to the invention therefore comprises the hydrocarbonylation/hydroformylation through synthesis gas, i.e. a mixture of carbon monoxide (CO) and hydrogen ($H_2$) in the presence of suitable catalysts and the reductive amination with amines in the presence of suitable catalysts of the general formula $HNR^1R^2$, wherein $R^1$ and $R^2$ are as defined above. The hydroaminomethylation in the presence of primary amines leads to secondary amines while the conversion with secondary amine components leads to tertiary amines. In the method according to the invention, diisopropylamine is preferably used as an amine component.

According to a design example of the method according to the invention, the substituent X represents hydroxy (OH). This allows, starting with 1,1-diarylether compounds, the hydroformylation to chrome/lactol systems according to the general graphic formula shown below

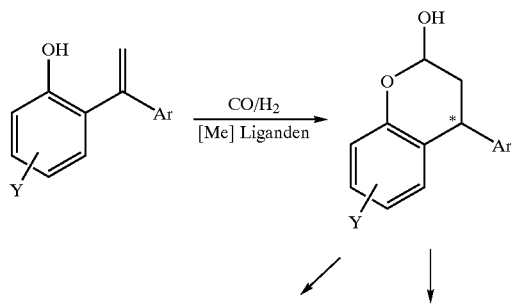

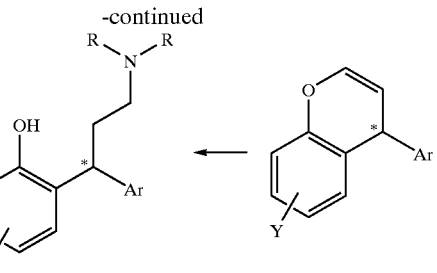

Liganden=ligands

These intermediate products are converted using known reactions into derivatives of the 2-[(3R)-3-(+)(diisopropylamino)-1-phenylpropyl]-4-(hydroxymethyl) phenol, its acylated compounds and salts. Accurate descriptions of these reactions are contained in EP 0 957 073.

Procedural rules for reductive amination of compounds of the lactol type are also contained in WO 99/58478.

The abovementioned 1,1-diarylethene compounds according to general formula II can be produced using known methods as, for example, described in Yamaguchi M; Arisawa M; Omata K; Kabuto K; Hirama M; Uchimaru T; Journal of Organic Chemistry 1998, 63(21), 7298–7305 and Yamaguchi M; Hayashi A; Hirama M; Journal of the American Chemical Society 1995, 117(3), 1151–2.

The method according to the invention is generally conducted at a temperature in the range 50 to 200° C. and preferably 100 to 140° C.

The reaction pressure here is between 40 and 200 bar and preferably between 80 and 120 bar.

For the hydroformylation, a mixture of carbon monoxide and hydrogen (synthesis gas) is used, wherein the ratio of carbon monoxide (CO) to hydrogen ($H_2$) is generally between 10/90 and 90/10 and preferably between 70/30 and 90/10.

The breadth of the pressure ratios is a result of the need to optimise the ratios between ligand and catalyst for each substrate separately and these are, therefore, dependent upon the substrate, catalyst preliminary stage and ligand, etc.

The reaction time is generally between 2 hours and 4 days and preferably in a range of between 1 and 3 days.

The abovementioned reaction times are influenced by the respective equipment set-up. With an optimum gas infeed, shorter reaction times can also be achieved.

The catalyst used in the method according to the invention includes one or more transition metals selected from the group comprising ruthenium, rhodium, platinum, cobalt, iridium, palladium and nickel, with preference being for rhodium.

According to a preferred embodiment of the method according to the invention, the catalyst is formed in-situ from a catalyst precursor and a ligand.

Suitable catalyst precursors are preferably $[Rh(cod)Cl]_2$ and/or $Rh(acac)(CO)_2$ or comparable rhodium complexes.

Suitable ligands are listed below along with the relevant abbreviation:
BINAPHOS=R-2-(diphenylphosphino)-1,1'-binaphthalen,-2'-yl-(S)-1,1'-binaphthalene-2,2'-diylphosphite,
DIOP=(2,2-dimethyl-4,5-diphenylphosphinomethyl)-1,3-dioxolane,
DIOP-DBP=(2,2-dimethyl-4,5-bis(5H-dibenzophosphol-5-ylmethyl)-1,3-dioxolane,
DPPB=1,4-bis(diphenylphosphino)butane,
CHIRAPHOS=2,3-bis(diphenylphosphino)butane,
CBDPP=1,2-bis(diphenylphosphinomethyl)cyclobutane,
CBDBP=1,2-bis(5H-dibenzophosphol-5-ylmethyl) cyclobutane, CHDPP=1,2-bis(diphenylphosphinomethyl)cyclohexane,
CHDBP=1,2-bis(5H-dibenzophosphol-5-ylmethyl) cyclohexane,
CHDPPO=1,2-bis(diphenylphosphinoxy)cyclohexane,
BzMePhP*=benzyl-methyl-phenylphosphine,
CAMP=cyclohexyl-o-anisyl-methylphosphine,
NMDPP=neomenthyldiphenylphosphine,
PAMP=phenyl-o-anisyl-methylphosphine,
BPPM=(2S, 4S)-N-tert.butoxycarbonyl-4-diphenylphosphino-2-diphenylphosphinomethylpyrrolidine,
o-DPPB=ortho-diphenylphosphanylbenzoyl,
PBu3=tributylphosphine,
BINAP=2,2'-bis-(diphenylphosphino)-1,1'-binaphthyl.

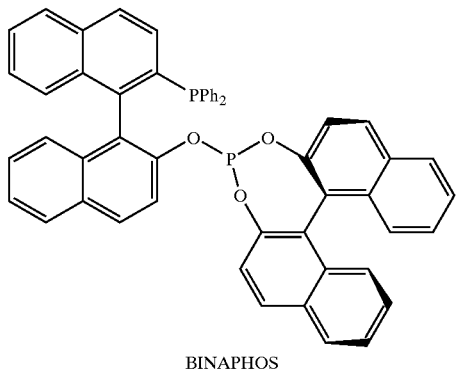

BINAPHOS

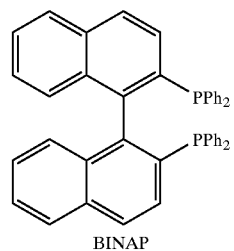

BINAP

Phosphite and binaphthyl compounds can also be used as ligands.

Preferred ligands are tributylphosphine, (+)- or (−)-(2,2-dimethyl-4,5-diphenylphosphinomethyl)-1,3-dioxolane, (R)- or (S)-BINAP and/or (R,S)-BINAPHOS.

If tributylphosphine is used as a ligand, then the ratio of ligand to rhodium is generally between 1:1 and 25:1 and preferably between 4:1 and 10:1.

When (R)- or (S)-BINAP is used, it is between 1:1 and 6:1 and preferably between 1:1 and 2:1.

Finally, for (R, S)-BINAPHOS it is between 1:1 and 6:1 and preferably between 1:1 and 2:1.

The method according to the invention is based, as already stated above, on the hydroaminomethylation of 1,1-diarylethenes using a suitable catalyst system. It has the advantage that it can be conducted as a one step reaction, allowing the direct isolation of the desired diarylpropylamine derivative.

The chirality centre in position 3 of the 3,3-diarylpropylamine derivative can be generated by a suitable choice of chiral ligands for the metallic catalyst centre in a stereoselective fashion (ligand control). If one of the aryl groups in the 1,1-diarylethene used as the starting material is substituted in the ortho-position by a heteroatom, that is modified with chiral groups, the chiral synthesis is controlled by the substrate (substrate control). This is comparable with homoallylalcohols, the conformation of which is predetermined by the planar aromates. Finally, the combination of these methods (ligand and substrate control) allows double stereo side differentiation.

The method according to the invention is further explained using the following examples. In these, the following definitions apply:
TLC Thin Layer Chromatography
HPLC High Performance Liquid Chromatography
NMR Nuclear Magnetic Resonance
° C. Degrees Celsius
RT Room Temperature
THF Tetrahydrofurane
acac Acetonylacetate
cod cis, cis-1,5-cyclooctadiene
abs. absolute
MTBE Methyl Tertiary Butyl Ether
h Hour(s)
TMS Tetra-Methyl-Silane Equipment List The NMR spectra are recorded using a DRX 400 from the Bruker company. TMS is used as an internal standard.

Mass spectres are measured on a Finnigan CA 5. The elemental composition is determined using a Leco CHNS-932.

Gas chromatographic investigations are carried out using a CarloErba GC-4160 with 25 m or with a Fisous GC-8130 with 30 m CP sil-5 capillaries.

EXAMPLE 1

Production of 2-methoxy-5-methyl-benzophenone

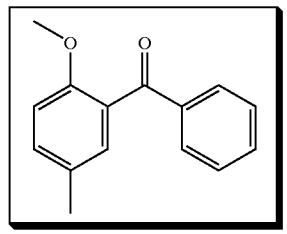

Preparation:
5.00 g (23.5 mmole) 2-hydroxy-5-methyl-benzophenone
6.67 g (47.1 mmole) methyliodide
4.50 g (32.6 mmole) potassium carbonate
50 ml abs. acetone
Method:
To a solution of 5.00 g (23.5 mmole) 2-hydroxy-5-methyl-benzophenone and 6.67 g (47.1 mmole) methyliodide in 50 ml abs. acetone 4.50 g (32.6 mmole) potassium carbonate are added. The reaction mixture is then heated for 5 hours with recycling. Following cooling, 50 ml water and 50 ml petroleum ether (30/60) are added to the suspension. The organic phase is separated off, the aqueous phase is extracted twice with 75 ml petroleum ether (30/60) and the purified organic phase is washed twice with 50 ml 10% NaOH solution. The organic phase is then dried through magnesium sulphate and the solvent is removed. 3.80 g (16.8 mmole, 71%) 2-methoxy-5-methyl-benzophenone are obtained.

Yield: 3.80 g (16.8 mmole, 71%) 2-methoxy-5-methyl-benzophenone $^1$H-NMR (400 MHz, CDCl$_3$): δ [ppm]=2.21 (s, 3H, CH$_3$), 3.56 (s, 3H, OCH$_3$), 6.77 (d, $^3$J=8.4 Hz, 1H, PhH), 7.06 (d, $^4J$=1.9 Hz, 1H, PhH), 7.15 (m, 1H, PhH), 7.31 (t, $^3J$=7.7 Hz, 2H, PhH), 7.43 (m, 1H, PhH), 7.71 (dd, $^3J$=8.3 Hz, $^2J$=1.2 Hz, 2H, PhH). $^{13}$C-NMR (100 MHz, CDCl$_3$): δ [ppm]=20.3 (CH$_3$), 55.6 (OCH$_3$), 111.4 (CH$_{arom}$), 128.1 (2×CH$_{arom}$), 128.5 (Cq$_{arom}$), 129.7 (2×CH$_{arom}$), 129.8 (Cq$_{arom}$), 129.9 (CH$_{arom}$), 132.2 (CH$_{arom}$), 132.8 (CH$_{arom}$), 137.8 (Cq$_{arom}$), 155.2 (Cq$_{arom}$), 196.6 (C=O).

EXAMPLE 2

Production of 2-benzyloxy-5-methyl-benzophenone

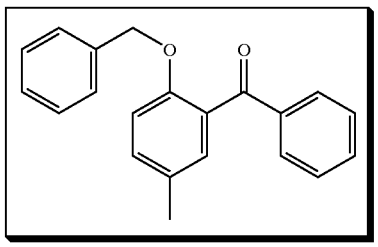

Preparation:

2.00 g (9.4 mmole) 2-hydroxy-5-methyl-benzophenone 1.66 g (9.7 mmole) benzyl bromide 1.73 g (12.5 mmole) potassium carbonate 12 ml abs. acetone Method:

To a solution of 2.00 g (9.4 mmole) 2-hydroxy-5-methyl-benzophenone and 1.66 g (9.7 mmole) benzyl bromide in 12 ml abs. acetone 1.73 g (12.5 mmole) potassium carbonate are added. The reaction mixture is then heated for 16 hours with recycling. Following cooling of the suspension, it is filtered and the residue is washed with 50 ml diethylether. Following removal of the solvent on the rotary evaporator, 2.74 g (9.1 mmole, 96%) 2-benzyloxy-5-methyl-benzophenone are obtained.

Yield: 2.74 g (9.1 mmole, 96%) 2-benzyloxy-5-methyl-benzophenone $^1$H-NMR (400 MHz, CDCl$_3$): δ [ppm]=2.31 (s, 3H, CH$_3$), 4.94 (s, 2H, OCH$_2$), 6.92 (m, 3H, PhH), 7.17 (m, 3H, PhH), 7.23 (m, 2H, PhH), 7.41 (t, $^3J$=7.6 Hz, 2H, PhH), 7.53 (m, 1H, PhH), 7.81 (m, 2H, PhH). $^{13}$C-NMR (100 MHz, CDCl$_3$): δ [ppm]=20.3 (CH$_3$), 70.1 (OCH$_2$), 112.8 (CH$_{arom}$), 126.5 (2×CH$_{arom}$), 127.4 (CH$_{arom}$), 128.2 (4×CH$_{arom}$), 129.1 (Cq$_{arom}$), 129.6 (2×CH$_{arom}$), 130.1 (CH$_{arom}$), 130.4 (Cq$_{arom}$), 132.4 (CH$_{arom}$), 132.6 (CH$_{arom}$), 136.5 (Cq$_{arom}$), 138.3 (Cq$_{arom}$), 154.3 (Cq$_{arom}$), 196.9 (C=O).

| Melting point: | 78° C. | |
|---|---|---|
| Elementary analysis: | | |
| theor.: | C 83.4 | H 6.0 |
| actual: | C 83.2 | H 5.8 |

EXAMPLE 3

Production of 1-methoxy-4-methyl-2-(1-phenyl-vinyl)-benzene

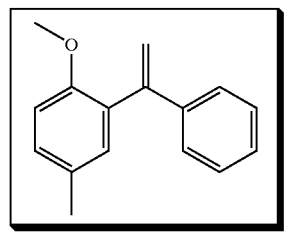

Preparation:

3.70 g (16.3 mmole) 2-methoxy-5-methyl-benzophenone 7.58 g (21.2 mmole) methyltriphenylphosphonium-bromide 17.0 ml (21.2 mmole) n-butyllithium (1.25M in n-hexane)

20 ml abs. THF

Method:

To a suspension of 7.58 g (21.2 mmole) methyltriphenylphosphoniumbromide in 15 ml abs. THF at room temperature within 10 minutes 17.0 ml (21.2) n-butyllithium (1.25M in n-hexane)are added dropwise. The reddish solution obtained is cooled to −78° C. and then within 15 minutes a solution of 3.70 g (16.3 mmole) 2-methoxy-5-methyl-benzophenone in 5 ml abs. THF is added. Agitation is performed initially for 20 minutes at −78° C. and for a further 8 h at room temperature. Then 80 ml water are added to the reaction mixture and extracted twice with 50 ml diethylether in each case. The purified organic phases are then dried through magnesium sulphate and the solvent is removed. Purification of the raw product obtained takes place by column chromatography on silica gel with toluene as the solvent. 3.03 g (13.5 mmole, 83%) 1-methoxy-4-methyl-2-(1-phenyl-vinyl)-benzene are obtained.

Yield: 3.03 g (13.5 mmole, 83%) 1-methoxy-4-methyl-2-(1-phenyl-vinyl)-benzene. $^1$H-NMR (400 MHz, CDCl$_3$): δ [ppm]=2.22 (s, 3H, CH$_3$), 3.51 (s, 3H, OCH$_3$), 5.22 (s, 1H, =CH$_2$), 5.63 (s, 1H, =CH$_2$), 6.71 (d, $^3J$=8.3 Hz, 1H, PhH), 6.97 (s, 1H, PhH), 7.01 (d, $^3J$=8.0 Hz, 1H, PhH), 7.16 (m, 5H, PhH). $^{13}$C-NMR (100 MHz, CDCl$_3$): δ [ppm]=20.4 (CH$_3$), 55.8 (OCH$_3$), 111.3 (CH$_{arom}$), 115.2 (=CH$_2$), 126.3 (2×CH$_{arom}$), 127.2 (CH$_{arom}$), 128.0 (2×CH$_{arom}$), 129.2 (CH$_{arom}$), 129.8 (Cq$_{arom}$), 130.8 (Cq$_{arom}$), 131.8 (CH$_{arom}$), 141.0 (Cq$_{arom}$), 147.0 (Cq$_{olefin}$), 155.0 (Cq$_{arom}$).

| Elementary analysis: | | |
|---|---|---|
| theor.: | C 85.7 | H 7.2 |
| actual: | C 85.7 | H 7.2 |

EXAMPLE 4

Production of 1-benzyloxy-4-methyl-2-(1-phenyl-vinyl)-benzene

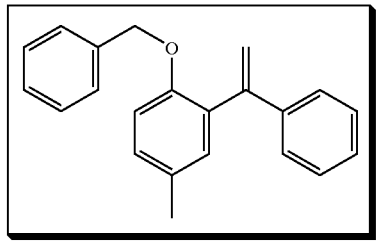

Preparation:

1.41 g (4.7 mmole) 2-benzyloxy-5-methyl-benzophenone 2.16 g (6.1 mmole) methyltriphenyl phosphoniumbromide 4.9 ml (6.1 mmole) n-butyllithium (1.25M in n-hexane)

17 ml abs. THF

Method:

Same as Example 3

Yield: 1.23 g (4.1 mmole, 88%) 1-benzyloxy-4-methyl-2-(1-phenyl-vinyl)-benzene. $^1$H-NMR (400 MHz, CDCl$_3$): δ [ppm]=2.32 (s, 3H, CH$_3$), 4.84 (s, 2H, OCH$_2$), 5.32 (d, $^3$J=1.4 Hz, 1H, =CH$_2$), 5.65 (d, $^3$J=1.4 Hz, 1H, =CH$_2$), 6.83 (m, 3H, PhH), 7.07–7.37 (m, 10H, PhH). $^{13}$C-NMR (100 MHz, CDCl$_3$): δ [ppm]=20.5 (CH$_3$), 70.1 (OCH$_2$), 112.5 (CH$_{arom}$), 115.5 (=CH$_2$), 126.5 (2×CH$_{arom}$), 126.8 (2×CH$_{arom}$), 127.2 (CH$_{arom}$), 127.3 (CH$_{arom}$), 128.1 (4×CH$_{arom}$), 129.3 (CH$_{arom}$), 130.1 (Cq$_{arom}$), 131.3 (Cq$_{arom}$), 132.1 (CH$_{arom}$), 137.1 (Cq$_{arom}$), 141.6 (Cq$_{arom}$), 147.6 (Cq$_{olefin}$), 153.9 (Cq$_{arom}$).

MS (EI, 70 eV): m/z [%]=300 (39, M$^+$), 285 (11), 262 (6), 251 (9), 209 (100), 200 (9), 195 (20), 181 (20), 165 (19), 115 (3), 91 (95), 65 (9).

| Elementary analysis: | | |
|---|---|---|
| theor.: | C 88.0 | H 6.7 |
| actual: | C 87.6 | H 6.7 |

EXAMPLE 5

Production of diisopropyl-[3-(2-methoxy-5-methylphenyl)-3-phenylpropyl]-amine

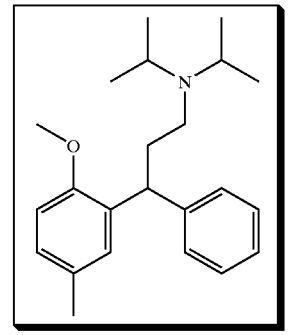

Preparation:

0.700 g (3.1 mmole) 1-methoxy-4-methyl-2-(1-phenyl-vinyl)-benzene 0.354 g (3.5 mmole) diisopropylamine see Table 1 catalyst precursor see Table 1 tributylphosphine 10 ml abs. dioxane Method:

0.700 g (3.1 mmole) 1-methoxy-4-methyl-2-(1-phenyl-vinyl)-benzene, 0.354 g (3.5 mmole) diisopropylamine, a defined quantity of catalyst precursor (see Table 1), a defined quantity of tributylphosphine (see Table 1) and 10 ml abs. dioxane are agitated in a pressure vessel in a CO/H$_2$ atmosphere under the conditions given in Table 1. Following cooling and relieving of the pressure vessel, the reaction solution undergoes absorptive filtering (eluant: MTBE) through aluminium oxide (activity II–III, basic). Following removal of the solvent, the cleaning of the raw product takes place by column chromatography on aluminium oxide (activity I, neutral) with petroleum ether (30/60)/MTBE=5/1 (v/v) as the eluant.

TABLE 1

Results of the hydroaminomethylation with 1-methoxy-4-methyl-2-(1-phenyl-vinyl)-benzene

| No. | PBu$_3$/Rh | T [° C.] | p (CO/H$_2$) [bar] | t [d] | hydr. educt [%]* | Product [%]* |
|---|---|---|---|---|---|---|
| 1** | 25/1 | 115 | 80/20 | 4 | — | — |
| 2** | 6/1 | 135 | 90/10 | 4 | approx. 1 | 38 (22) |
| 3** | 6/1 | 140 | 90/10 | 5 | 11 | 49 (37) |
| 4*** | 16/1 | 110 | 90/10 | 3 | approx. 2 | 12 |
| 5*** | 8/1 | 130 | 90/10 | 3 | 6 | 85 |
| 6*** | — | 130 | 90/10 | 3 | 11 | 70 |

*GC proportions (values in brackets correspond to isolated yields)
**[Rh(cod)Cl]$_2$ (0.5 mol-% with reference to olefin)
***Rh(acac) (CO)$_2$ (1 mol-% with reference to olefin)

$^1$H-NMR (400 MHz, CDCl$_3$): δ [ppm]=0.92 (d, $^3$J=6.5 Hz, 6H, 2×CHCH$_3$), 0.92 (d, $^3$J=6.5 Hz, 6H, 2×CHCH$_3$), 2.12 (m, 2H, CHCH$_2$), 2.25 (s, 3H, PhCH$_3$), 2.33 (m, 2H, NCH$_2$), 2.96 (sept, $^3$J=6.5 Hz, 2H, 2×CHMe$_2$), 3.72 (s, 3H, OCH$_3$), 4.34 (t, $^3$J=7.6 Hz, 1H, CHPh$_2$), 6.69 (d, $^3$J=8.3 Hz, 1H, PhH), 6.92 (dd, $^3$J=8.1 Hz, $^4$J=1.9 Hz, 1H, PhH), 7.05 (d, $^4$J=1.9 Hz, 1H, PhH), 7.12 (t, $^3$J=7.0 Hz, 1H, PhH), 7.13–7.24 (m, 4H, PhH). $^{13}$C-NMR (100 MHz, CDCl$_3$): δ

[ppm]=20.5 (2×CHCH₃), 20.7 (2×CHCH₃), 20.7 (PhCH₃), 37.0 (CHCH₂), 41.3 (PhCH), 44.1 (NCH₂), 48.7 (2×NCH), 55.5 (OCH₃), 110.6 (CH$_{arom}$), 125.6 (CH$_{arom}$), 127.1 (CH$_{arom}$), 128.0 (2×CH$_{arom}$), 128.2 (2×CH$_{arom}$), 128.3 (CH$_{arom}$), 129.5 (Cq$_{arom}$), 133.4 (Cq$_{arom}$), 145.1 (Cq$_{arom}$), 154.9 (Cq$_{arom}$). GC-MS (EI, 70EV): m/z [%]=340 (M⁺+1, 45), 324 (6), 296 (1), 211 (3), 126 (3), 114 (100), 100 (20), 91 (7), 72 (13).

| Elementary analysis: C₂₃H₃₃NO (339.26) | | | |
|---|---|---|---|
| theor.: | C 81.4 | H 9.8 | N 4.1 |
| actual: | C 80.9 | H 9.4 | N 4.3 |

EXAMPLE 6

Production of 3-(2-benzyloxy-5-methylphenyl)-3-phenylpropyl]-diisopropylamine

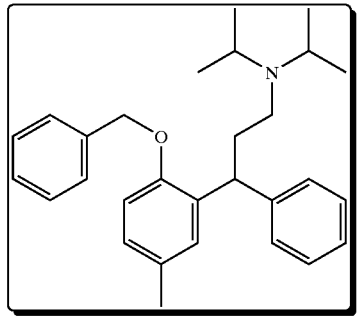

Preparation:

0.601 g (2.00 mmole) 1-benzyloxy-4-methyl-2-(1-phenyl-vinyl)-benzene 0.229 g (2.26 mmole) diisopropylamine 5.2 mg (0.02 mmole) Rh(acac)(CO)₂ see Table 2 tributylphosphine 10 ml abs. dioxane Method:
Same as Example 5

TABLE 2

Results of the hydroaminomethylation with 1-benzyloxy-4-methyl-2-(1-phenyl-vinyl)-benzene

| No. | PBu₃/Rh | T [° C.] | p (CO/H₂) [bar] | t [d] | Product [%]* |
|---|---|---|---|---|---|
| 7** | 8/1 | 130 | 90/10 | 3 | 84 (79) |
| 8** | 2/1 | 100 | 90/10 | 3 | 4 |
| 9** | — | 130 | 90/10 | 1 | 49 |
| 10** | — | 130 | 90/10 | 3 | 76 |

*GC proportions (value in brackets corresponds to isolated yield)
**Rh(acac) (CO)₂ (1 mol-% with reference to olefin)

¹H-NMR (400 MHz CDCl₃): δ [ppm]=0.90 (d, ³J=6.5 Hz, 12H, 4×CHCH₃), 2.13 (m, 2H, CHCH₂), 2.26 (s, 3H, PhCH₃), 2.33 (m, 2H, NCH₂), 2.94 (sept, ³J=6.5 Hz, 2H, 2×CHMe₂), 4.39 (t, ³J=7.7 Hz, 1H, CHPh₂), 4.94 (d, ²J=15.5 Hz , 1H, OCH₂), 4.97 (d, ²J=15.5 Hz , 1H, OCH₂), 6.73 (d, ³J=8.2 Hz, 1H, PhH), 6.91 (dd, ³J=8.2 Hz, ⁴J=1.7 Hz, 1H, PhH), 7.10–7.36 (m, 11H, PhH). ¹³C-NMR (100 MHz, CDCl₃): δ [ppm]=20.5 (2×CHCH₃), 20.6 (2×CHCH₃), 20.7 (PhCH₃), 37.0 (CHCH₂), 41.5 (PhCH), 44.1 (NCH₂), 48.8 (2×NCH), 70.1 (OCH₂), 111.7 (CH$_{arom}$), 125.6 (CH$_{arom}$), 127.1 (CH$_{arom}$), 127.3 (2×CH$_{arom}$), 127.6 (CH$_{arom}$), 128.0 (2×CH$_{arom}$), 128.3 (2×CH$_{arom}$), 128.3 (2×Ch$_{arom}$), 128.4 (CH$_{arom}$), 129.8 (Cq$_{arom}$), 133.6 (Cq$_{arom}$), 137.5 (Cq$_{arom}$), 145.1 (Cq$_{arom}$), 153.9 (Cq$_{arom}$). MS (EI, 70EV): m/z [%]= 415 (M⁺, 23), 400 (25), 339 (4), 324 (6), 287 (1), 223 (3), 197 (3), 165 (1), 114 (100), 99 (4), 91 (18), 72 (11).

| Elementary analysis: (C₂₉H₃₇NO, M = 415.29) | | | |
|---|---|---|---|
| theor.: | C 83.8 | H 9.0 | N 3.4 |
| actual: | C 84.0 | H 9.0 | N 3.4 |

EXAMPLE 7

Production of 4-hydroxy-3-(1-phenyl-vinyl)-benzoic acid ethylester

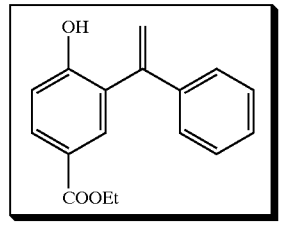

Preparation:

4.98 g (30 mmole) p-hydroxybenzoic acid ethylester 3.06 g (30 mmole) phenylacetylene 31.26 g (120 mmole) tin tetrachloride 22.24 g (120 mmole) tributylamine 150 ml 1,2-dichlorethane Method:

Under an argon atmosphere, a solution of 4.98 g (30 mmole) phydroxy-benzoic acid ethylester, 3.06 g (30 mmole) phenylacetylene, 31.26 g (120 mmole) tin tetrachloride and 22.24 (120 mmole) tributylamine in 150 ml 1,2-dichlorethane are heated for 1 h with recycling. Then 60 ml 4 M KOH and 30 ml ethanol are added to the reaction mixture and heated for 1 h with recycling. Following cooling, the solution is acidified with 4 M HCl and extracted twice with 150 ml diethylether each time. The purified organic phases are dried through MgSO₄ and the solvent is removed on the rotary evaporator. The remaining residue undergoes absorptive filtering (silica gel, MTBE) and the raw product obtained in this way is cleaned by column chromatography (silica gel, toluene/MTBE=8/1 (v/v)). 2.63 g (9.8 mmole, 33%) 4-hydroxy-3-(1-phenyl-vinyl)-benzoic acid-ethylester are obtained.

Yield: 2.63 g (9.8 mmole, 33%) 4-hydroxy-3-(1-phenyl-vinyl)-benzoic acid-ethylester. ¹H-NMR (400 MHz, CDCl₃): δ [ppm]=1.36 (t, ³J=7.1 Hz, 3H, CH₃), 4.33 (q, ³J=7.1 Hz, 2H, OCH₂), 5.44 (d, ²J=0.9 Hz, 1H, =CH₂), 5.91 (d, ²J=0.9 Hz, 1H, =CH₂), 6.97 (d, ³J=8.5 Hz, 1H, PhH), 7.34 (m, 5H, PhH), 7.89 (d, ⁴J=2.1 Hz, 1H, PhH), 7.96 (dd, ³J=8.5 Hz, ⁴J=2.1 Hz, 1H, PhH). ¹³C-NMR (100 MHz, CDCl₃): δ [ppm]=14.3 (CH₃), 60.8 (OCH₂), 115.8 (CH$_{arom}$), 117.5 (=CH₂), 122.9 (Cq$_{arom}$), 126.9 (2×CH$_{arom}$) 127.5 (Cq$_{arom}$), 128.8 (3×CH$_{arom}$), 131.3 (CH$_{arom}$), 132.3 (CH$_{arom}$), 138.7 (Cq$_{arom}$), 144.3 (Cq$_{olefin}$), 157.1 (Cq$_{arom}$), 166.3 (COOEt). MS (EI, 70EV): m/z [%]=268 (M⁺, 98), 267 (100), 253 (35) 239 (32), 225 (13), 223 (24), 194 (6), 165 (20), 152 (12), 115 (5), 111 (6), 104 (7).

EXAMPLE 8

Production of 4-benzyloxy-3-(1-phenyl-vinyl)-benzoic acid ethylester

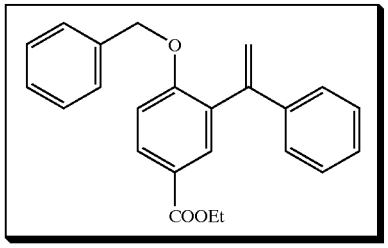

Preparation:

0.990 g (3.7 mmole) 4-hydroxy-3-(1-phenyl-vinyl)-benzoic acid ethylester 0.652 g (3.8 mmole) benzyl bromide 0.680 g (4.9 mmole) potassium carbonate 7 ml abs. acetone Method:

To a solution of 0.990 g (3.7 mmole) 4-hydroxy-3-(1-phenylvinyl)-benzoic acid ethylester and 0.652 g (3.8 mmole) benzyl bromide in 7 ml abs. acetone 0.680 g (4.9 mmole) potassium carbonate are added. The reaction mixture is then heated for 4 hours with recycling. Following cooling of the suspension it is filtered and the radical is washed with 50 ml diethtylether. Following removal of the solvent on the rotary evaporator, 1.280 g (3.6 mmole, 97%) 4-benzyloxy-3-(1-phenyl-vinyl)-benzoic acid ethylester are obtained as a colourless oil.

Yield: 1.280 g (3.6 mmole, 97%) 4-benzyloxy-3-(1-phenyl-vinyl)-benzoic acid-ethylester. $^1$H-NMR (400 MHz, CDCl$_3$): δ [ppm]=1.38 (t, $^3$J=7.1 Hz, 3H, CH$_3$), 4.36 (q, $^3$J=7.1 Hz, 2H, OCH$_2$CH$_3$), 4.93 (s, 2H, OCH$_2$Ph), 5.36 (d, $^2$J=1.2 Hz, 1H, =CH$_2$), 5.70 (d, $^2$J=1.2 Hz, 1H, =CH$_2$), 6.80 (dd, $^3$J=7.6 Hz, $^4$J=1.6 Hz, 2H, PhH), 6.94 (d, $^3$J=9.3 Hz, 1H, PhH), 7.18 (m, 3H, PhH), 7.29 (m, 5H, PhH), 8.03 (m, 2H, PhH). $^{13}$C-NMR (100 MHz, CDCl$_3$): δ [ppm]=14.4 (CH$_3$), 60.7 (OCH$_2$CH$_3$), 69.9 (OCH$_2$Ph), 111.4 (CH$_{arom}$), 116.3 (=CH$_2$), 123.0 (Cq$_{arom}$), 126.4 (2×CH$_{arom}$), 126.7 (2×CH$_{arom}$), 127.4 (CH$_{arom}$), 127.6 (CH$_{arom}$), 128.2 (4×CH$_{arom}$), 131.2 (CH$_{arom}$), 131.3 (Cq$_{arom}$), 132.8 (CH$_{arom}$), 136.0 (Cq$_{arom}$), 141.0 (Cq$_{arom}$), 146.8 (Cq$_{olefin}$), 159.6 (Cq$_{arom}$), 166.3 (COOEt). MS (EI, 70 eV): m/z [%]=358 (37, M⁺), 343 (9), 329 (6), 313 (10), 285 (13), 267 (95), 253 (11), 239 (6), 207 (3), 194 (12), 165 (14), 139 (2), 105 (3), 91 (100), 65 (10).

EXAMPLE 9

Production of 4-benzyloxy-3-(3-diisopropylamino-1-phenyl-propyl)-benzoic acid ethylester

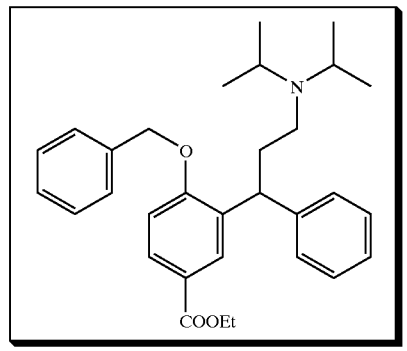

Preparation:

1.222 g (3.41 mmole) 4-benzyloxy-3-(1-phenyl-vinyl)-benzoic acid ethylester 0.390 g (3.85 mmole) diisopropylamine 8.8 mg (0.03 mmole) Rh(acac)(CO)$_2$ 68 μl (0.27 mmole) tributylphosphine 15 ml abs. dioxane Method:

Same as example 5 with p(CO/H$_2$)=90/10 bar, 130° C., 65 h. Cleaning of the raw product takes place by column chromatography (silica gel, petroleum ether/MTBE/Net$_3$ (solvent mixture with increasing polarity; PE/MTBE=1/1→PE/MTBE/NEt$_3$=5/5/1).

Yield: 1.155 g (2.4 mmole, 72%) 4-benzyloxy-3-(3-diisopropylamino-1-phenyl-propyl)-benzoic acid ethylester. $^1$H-NMR (400 MHz, CDCl$_3$): δ [ppm]=0.90 (*t, $^3$J=6.3 Hz, 12H, 4×CHCH$_3$), 1.37 (t, $^3$J=7.1 Hz, 3H, CH$_2$CH$_3$), 2.17 (m, 2H, CHCH$_2$), 2.33 (m, 2H, NCH$_2$), 2.95 (sept, $^3$J=6.3 Hz, 2H, 2×CHMe$_2$), 4.36 (m, 3H, CHPh$_2$, CH$_2$CH$_3$), 5.02 (d, $^2$J=15.3 Hz, 1H, OCH$_2$Ph), 5.05 (d, $^2$J=15.3 Hz, 1H, OCH$_2$Ph), 6.85 (d, $^3$J=8.6 Hz, 1H, PhH), 7.16 (m, 1H, PhH), 7.20–7.25 (m, 6H, PhH), 7.32 (m, 3H, PhH), 7.87 (dd, $^3$J=8.6 Hz, $^4$J=2.1 Hz, 1H, PhH), 8.09 (d, $^4$J=2.1 Hz, 1H, PhH). $^{13}$C-NMR (100 MHz, CDCl$_3$): δ [ppm]=14.4 (CH$_2$CH$_3$) 20.5 (2×CHCH$_3$), 20.6 (2×CHCH$_3$), 36.6 (CHCH$_2$), 41.7 (PhCH), 43.9 (NCH$_2$), 48.6 (2×NCH), 60.6 (CH$_2$CH$_3$), 70.0 (OCH$_2$Ph), 111.0 (CH$_{arom}$), 122.7 (Cq$_{arom}$), 125.8 (CH$_{arom}$), 127.4 (2×CH$_{arom}$), 127.9 (CH$_{arom}$), 128.0 (2×CH$_{arom}$), 128.2 (2×CH$_{arom}$), 128.4 (2×CH$_{arom}$), 129.1 (CH$_{arom}$), 129.3 (CH$_{arom}$), 133.5 (Cq$_{arom}$), 136.3 (Cq$_{arom}$), 144.5 (Cq$_{arom}$), 159.7 (Cq$_{arom}$), 166.6 (COOEt). MS (EI, 70EV): m/z [%]=473 (M⁺, 15), 458 (23), 428 (2), 360 (3), 345 (2), 267 (4), 165 (2), 114 (100), 91 (41), 72 (90).

EXAMPLE 10

Production of 4-hydroxy-3-(1-phenyl-vinyl)-benzoic acid methylester

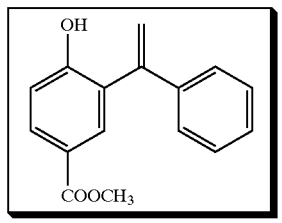

Preparation:

4.56 g (30 mmole) p-hydroxybenzoic acid methylester
6.13 g (60 mmole) phenylacetylene
31.26 g (120 mmole) tin tetrachloride
22.24 g (120 mmole) tributylamine
150 ml 1,2-dichlorethane
Method: Same as Example 7

Yield: 2.67 g (10.5 mmole, 35%) 4-hydroxy-3-(1-phenyl-vinyl)-benzoic acid-methylester. $^1$H-NMR (400 MHz, CDCl$_3$): δ [ppm]=3.84 (s, 3H, CH$_3$), 5.42 (d, $^2$J=1.0 Hz, 1H, =CH$_2$), 5.88 (d, $^2$J=1.0 Hz, 1H, =CH$_2$), 6.97 (d, $^3$J=8.5 Hz, 1H, PhH), 7.32 (m, 5H, PhH), 7.88 (d, $^4$J=2.3 Hz, 1H, PhH), 7.94 (dd, $^3$J=8.5 Hz, $^4$J=2.3 Hz, 1H, PhH). $^{13}$C-NMR (100 MHz, CDCl$_3$): δ [ppm]=51.9 (CH$_3$), 115.8 (CH$_{arom}$), 117.4 (=CH$_2$), 122.4 (Cq$_{arom}$), 126.8 (2×CH$_{arom}$), 127.6 (Cq$_{arom}$), 128.7 (CH$_{arom}$), 128.7 (2×CH$_{arom}$), 131.3 (CH$_{arom}$), 132.4 (CH$_{arom}$), 138.8 (Cq$_{arom}$), 144.3 (Cq$_{olefin}$), 157.3 (Cq$_{arom}$), 166.8 (COOMe). MS (EI, 70EV): m/z [%]=254 (M$^+$, 5), 253 (7), 239 (3), 223 (1), 165 (1), 152 (1), 131 (1), 120 (22), 105 (44), 91 (100), 77 (37), 65 (13), 59 (16), 51 (20), 45 (17).

EXAMPLE 11

Production of 4-benzyloxy-3-(1-phenyl-vinyl)-benzoic acid-methylester

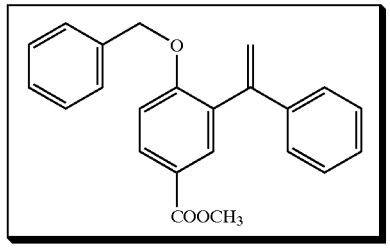

Preparation:

1.50 g (5.9 mmole) 4-hydroxy-3-(1-phenyl-vinyl)-benzoic acid methyl-ester
1.04 g (6.1 mmole) benzyl bromide
1.24 g (8.9 mmole) potassium carbonate
10 ml abs. acetone
Method:

To a solution of 1.50 g (5.9 mmole) 4-hydroxy-3-(1-phenyl-vinyl)-benzoic acid methylester and 1.04 g (6.1 mmole) benzyl bromide in 10 ml abs. acetone 1.24 g (8.9 mmole) potassium carbonate are added. The reaction mixture is then heated for 4 hours with recycling. Following cooling of the suspension, it is filtered and the residue is washed with 50 ml diethtylether. The solvent is removed and the raw product obtained is cleaned by column chromatography (silica gel, petroleum ether/MTBE=5/1 (v/v)). 1.62 g (4.7 mmole, 80%) 4-benzyloxy-3-(1-phenyl-vinyl)-benzoic acid-methylester are obtained.

Yield: 1.62 g (4.7 mmole, 80%) 4-benzyloxy-3-(1-phenyl-vinyl)-benzoic acid-methylester. $^1$H-NMR (400 MHz, CDCl$_3$): δ [ppm]=3.89 (s, 3H, CH$_3$), 4.93 (s, 2H, OCH$_2$), 5.36 (d, $^2$J=1.1 Hz, 1H, =CH$_2$), 5.70 (d, $^2$J=1.1 Hz, 1H, =CH$_2$), 6.80 (dd, $^3$J=7.6 Hz, $^4$J=1.6 Hz, 2H, PhH), 6.95 (d, $^3$J=9.0 Hz, 1H, PhH), 7.18 (m, 3H, PhH), 7.29 (m, 5H, PhH), 8.04 (m, 2H, PhH). $^{13}$C-NMR (100 MHz, CDCl$_3$): δ [ppm]=51.9 (CH$_3$), 69.9 (OCH$_2$), 111.5 (CH$_{arom}$), 116.3 (=CH$_2$), 122.7 (Cq$_{arom}$), 126.4 (2×CH$_{arom}$), 126.7 (2×CH$_{arom}$), 127.4 (CH$_{arom}$), 127.6 (CH$_{arom}$), 128.2 (4×CH$_{arom}$), 131.3 (CH$_{arom}$, Cq$_{arom}$), 132.8 (CH$_{arom}$), 136.0 (Cq$_{arom}$), 141.0 (Cq$_{arom}$), 146.7 (Cq$_{olefin}$), 159.7 (Cq$_{arom}$), 166.8 (COOMe). Melting point: 77–78° C.

EXAMPLE 12

Production of 4-benzyloxy-3-(3-diisopropylamino1-phenyl-propyl)-benzoic acid methylester

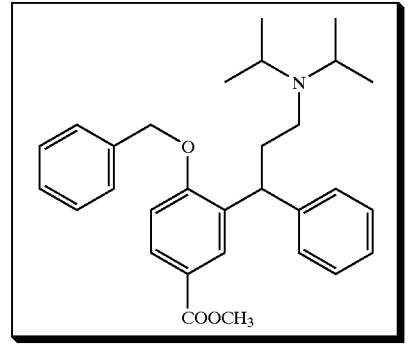

Preparation:

1.50 g (4.3 mmole) 4-benzyloxy-3-(1-phenyl-vinyl)-benzoic acid methylester
0.45 g (4.9 mmole) diisopropylamine
11.2 mg (0.04 mmole) Rh(acac)(CO)$_2$
86 μl (0.34 mmole) tributylphosphine
15 ml abs. dioxane
Method:

Same as example 5 with p (CO/H$_2$)=90/10 bar, 130° C., 65 h Cleaning of the raw product takes place by column chromatography (silica gel, petroleum ether/MTBE/Net$_3$ (solvent mixture with increasing polarity; PE/MTBE=1/1→PE/MTBE/NEt$_3$=5/5/1).

Yield: 1.262 g (2.75 mmole, 63%) 4-benzyloxy-3-(3-diisopropylamino-1-phenyl-propyl)benzoic acid methylester. $^1$H-NMR (400 MHz, CDCl$_3$): δ [ppm]=0.89 (d, $^3$J=6.5 Hz, 6H, 2×CHCH$_3$), 0.90 (d, $^3$J=6.5 Hz, 6H, 2×CHCH$_3$), 2.17 (m, 2H, CHCH$_2$), 2.33 (m, 2H, NCH$_2$), 2.95 (sept, $^3$J=6.5 Hz, 2H, 2×CHMe$_2$), 3.87 (s, 3H, OCH$_3$), 4.39 (t, $^3$J=7.6 Hz, 1H, CHPh$_2$), 5.02 (d, $^2$J=15.6 Hz, 1H, OCH$_2$Ph), 5.05 (d, $^2$J=15.6 Hz, 1H, OCH$_2$Ph), 6.85 (d, $^3$J=8.5 Hz, 1H, PhH), 7.14 (m, 1H, PhH), 7.20–7.25 (m, 6H, PhH), 7.32 (m, 3H, PhH), 7.86 (dd, $^3$J=8.5 Hz, $^4$J=2.1 Hz, 1H, PhH), 8.09 (d, $^4$J=2.1 Hz, 1H, PhH). $^{13}$C-NMR (100 MHz, CDCl$_3$): δ [ppm]=20.5 (2×CHCH$_3$), 20.6 (2×CHCH$_3$), 36.6 (CHCH$_2$), 41.6 (PhCH), 43.8 (NCH$_2$), 48.6 (2×NCH), 51.8 (OCH$_3$), 70.0 (OCH$_2$Ph), 111.0 (CH$_{arom}$), 122.3 (Cq$_{arom}$), 125.8

($CH_{arom}$), 127.4 (2×$CH_{arom}$), 127.9 ($CH_{arom}$), 128.0 (2×$CH_{arom}$), 128.3 (2×$CH_{arom}$), 128.4 (2×$CH_{arom}$), 129.1 ($CH_{arom}$), 129.4 ($CH_{arom}$), 133.6 ($Cq_{arom}$), 136.3 ($Cq_{arom}$), 144.4 ($Cq_{arom}$), 159.8 ($Cq_{arom}$), 167.0 (COOMe). MS (EI, 70EV): m/z [%]=459 ($M^+$, 32), 444 (49), 428 (3), 416 (1), 267 (2), 241(2), 209 (2), 165 (2), 114 (100), 91 (28), 72 (18), 57 (7). Melting point: 84° C.

| Elementary analysis: ($C_{30}H_{37}NO_3$, M = 459.28) | | | |
|---|---|---|---|
| theor.: | C 78.4 | H 8.1 | N 3.0 |
| actual: | C 78.4 | H 7.8 | N 2.9 |

EXAMPLE 13

Hydroformylation of 4-methyl-2-(1-phenyl-vinyl)-phenol

Preparation: 0.421 g (2.0 mmole) 4-methyl-2-(1-phenyl-vinyl)-phenol 5.0 mg (0.01 mmole) [RhCl(cod)]2

10 ml abs. dioxane

Method:

0.421 g (2.0 mmole) 4-methyl-2-(1-phenyl-vinyl)-phenol, 5.0 mg (0.01 mmole) [RhCl(cod)]$_2$ and 10 ml abs. dioxane are agitated in a pressure vessel for 3 days at 120° C. and under a pressure of 50 bar synthesis gas (CO:$H_2$=3.2). Following cooling and relieving of the pressure vessel, the reaction solution undergoes absorptive filtering (eluant: diethylether) through aluminium oxide (activity II–III, basic). Following removal of the solvent, the cleaning of the raw product takes place by column chromatography on silica gel with toluene/MTBE (volume ratio=3/1) as the eluant. 310 mg (1.3 mmole, 64%) 4-methyl-2-(1-phenyl-vinyl)-phenol are obtained as a mixture of two diastereomers at a ratio of 4:1.

Yield: 310 mg (1.3 mmole, 64%) 6-methyl-4-phenyl-chroman-2-ol.

Spectroscopic Data: 6-methyl-4-phenyl-chroman-2-ol.

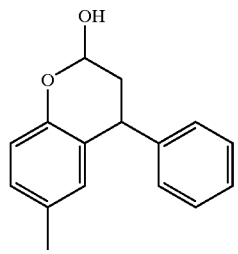

$^1$H-NMR (400 MHz, CDCl$_3$): δ [ppm]=2.06 (m, 4 H, CH$_3$+CHH), 2.17 (ddd, $^3$J=13.6 Hz, $^3$J=5.8 Hz, $^2$J=3.8 Hz, 1 H, CHH), 4.21 (dd, $^3$J=10.8 Hz, $^3$J=5.8 Hz, 1 H, CHArAr'), 5.41/5.54 (m, 1 H, CHOH), 6.50 (s, 1 H, PhH), 6.70 (m, 1 H, PhH), 6.85 (m, 1 H, PhH), 7.10–7.26 (m, 5 H, PhH). $^{13}$C-NMR (100 MHz, CDCl$_3$): δ [ppm]=20.5 (CH$_3$), 36.3 (CH$_2$), 36.9 (CHArAr'), 91.2/90.7 (CHOH), 116.5/116.6 (CH$_{arom}$), 124.8/124.7 (Cq$_{arom}$), 126.6/126.8 (CH$_{arom}$), 128.5/128.7 (2×CH$_{arom}$), 128.5/128.4 (CH$_{arom}$), 128.8/128.4 (2×CH$_{arom}$) 129.8/129.5 (CH$_{arom}$), 130.1/130.2 (Cq$_{arom}$), 144.4/144.0 (Cq$_{arom}$), 149.6/151.1 (Cq$_{arom}$).

The lactol obtained can be converted using known methods to the desired diarylpropylamines by reductive amination.

EXAMPLE 14

Hydroaminomethylation of 1-benzyloxy-4-methyl-2-(1-phenyl-vinyl)-benzene with chiral ligands Preparation: 0.250 g (0.83 mmole) 1-benzyloxy-4-methyl-2-(1-phenyl-vinyl)-benzene 0.095 g (0.94 mmole) diisopropylamine 4.3 mg (0.02 mmole) Rh(acac)(CO)$_2$ see Table 4 Ligand 10 ml abs. dioxane Method:

0.250 g (0.83 mmole) 1-benzyloxy-4-methyl-2-(1-phenyl-vinyl)-benzene, 0.095 g (0.94 mmole) diisopropylamine, 4.3 mg (0.02 mmole) Rh(acac)(CO)$_2$, a defined quantity of ligand (see Table 4) and 10 ml abs. dioxane are agitated in a pressure vessel under the conditions given in Table 4. Following cooling and relieving of the pressure vessel, the reaction solution undergoes absorptive filtering (eluant: MTBE) through aluminium oxide (activity II–III, basic). Following removal of the solvent, the cleaning of the raw product takes place by column chromatography on aluminium oxide (activity II–III, neutral) with cyclohexane/MTBE (ratio of volumes=5/1) as the eluant.

TABLE 4

Hydroaminomethylation with 1-benzyloxy-4-methyl-2-(1-phenyl-vinyl)-benzene using chiral diphosphine ligands

| No. | Ligand | L/Rh | CO/$H_2$ [bar] | T [ba | t [d] | Produc [%]* | $[α]_D^{20}$ [°] | ee** [%] |
|---|---|---|---|---|---|---|---|---|
| 3 | (R)-BINAP | 4/1 | 90/10 | 130 | 3 | 57 | +0.54 | <2 |
| 4 | (R)-BINAP | 4/1 | 90/10 | 130 | 1 | 58 | +0.53 | <2 |
| 5 | (R)-BINAP | 2/1 | 70/30 | 115 | 3 | 60 | +0.26 | <2 |
| 6 | (R)-BINAP | 2/1 | 60/20 | 105 | 3 | 45 | +0.28 | <2 |

*GC proportions
**hydrated educt is only detectable to a minor extent in each case (<5%)

EXAMPLE 15

Production of 4-[4-methyl-2-(1-phenyl-vinyl)-phenoxy]-3,5-dioxa-4-phospha-cyclohepta[2,1-a-3,4-a']dinaphthaline Preparation: 0.50 g (2.4 mmole) 1-hydroxy-4-methyl-2-(1-phenyl-vinyl)-benzene 1.05 g (3.0 mmole) (S)-(1,1-binaphthalene-2,2'-dioxy)-chloro-phosphine 0.33 g (3.3 mmole) triethylamine 55 ml diethylether Method:

To a solution of 0.50 g (2.4 mmole) 1-hydroxy-4-methyl-2-(1-phenyl-vinyl)-benzene and 1.05 g (3.0 mmole) (S)-(1,1-binaphthalene-2,2'-dioxy)chloro-phosphine in 45 ml diethylether at 0° C. 0.33 g (3.3 mmole) triethylamine in 10 ml diethylether are added. The suspension obtained in this way is agitated for 18 h at RT and then quenched with 50 ml brine. The organic phase is separated off and the aqueous phase is extracted twice with 50 ml diethylether each time. The purified organic phases are dried through MgSO$_4$ and the solvent is then removed on the rotary evaporator. The cleaning is carried out by column chromatography on silica gel with cyclohexane/ethylacetate (ratio 2/1) as the eluant. 0.73 g (1.4 mmole, 59%) 4-[4-methyl-2-(1-phenyl-vinyl)-phenoxy]-3,5-dioxa-4-phospha-cyclohepta[2,1-a-3,4-a'] dinaphthaline are obtained as a white solid matter.

Yield: 0.73 g (1.4 mmole, 59%) 4-[4-methyl-2-(1-phenyl-vinyl)-phenoxy]-3,5-dioxa-4-phospha-cyclohepta[2,1-a-3,4-a']dinaphthaline.

Spectroscopic Data: 4-[4-methyl-2-(1-phenyl-vinyl)-phenoxy]-3,5-dioxa-4-phospha-cyclohepta[2,1-a-3,4-a'] dinaphthalene

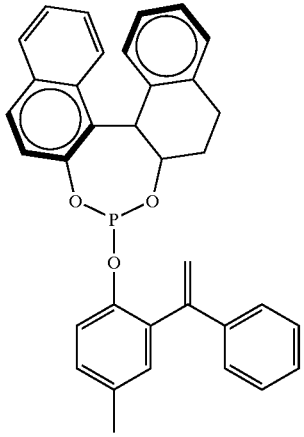

$^1$H-NMR (400 MHz, CDCl$_3$): δ [ppm]=2.33 (s, 3 H, CH$_3$), 5.35 (d, $^2$J=1.0 Hz, 1H =CH$_2$), 5.79 (d, $^2$J=1.0 Hz, 1 H, =CH$_2$), 7.02 (d, $^3$J=8.8 Hz, 1H, PhH), 7.13 (m, 3 H, PhH), 7.20 (m, 2 H, PhH), 7.28–7.38 (m, 10 H, PhH), 7.75 (d, $^3$J=8.8 Hz, 1 H, PhH), 7.87 (m, 3 H, PhH). $^{13}$C-NMR (100 MHz, CDCl$_3$): δ [ppm]=20.7 (CH$_3$), 116. 9 (=CH$_2$), 121.1 (2×CH$_{arom}$), 121.8 (CH$_{arom}$), 124.8 (CH$_{arom}$), 126.1 (2×CH$_{arom}$), 126.8 (2×CH$_{arom}$), 126.9 (2×CH$_{arom}$), 127.7 (CH$_{arom}$), 128.2 (2×CH$_{arom}$), 128.4 (2×CH$_{arom}$), 129.6 (2×CH$_{arom}$), 130.2 (CH$_{arom}$), 131.3 (2×Cq$_{arom}$), 132.2 (2×CH$_{arom}$), 132.6 (2×Cq$_{arom}$), 134.1 (Cq$_{arom}$), 134.2 (Cq$_{arom}$), 140.5 (Cq$_{arom}$), 146.1 (2×Cq$_{arom}$), 146.7 (Cq$_{arom}$, $^2$J$_{P-C}$=7.8 Hz), 147.0 (Cq$_{olefin}$), 147.7 (2×Cq$_{arom}$, $^2$J$_{P-C}$=4.9 Hz). $^{31}$P-NMR (202 MHz, CDCl$_3$): δ [ppm]=158.6

MS (EI, 70EV): m/z [%]=524 (M$^+$, 100), 447 (13), 315 (13), 268 (59), 239 (42), 209 (7), 105 (5), 77 (2). Melting point: 95° C.

EXAMPLE 16

Production of 2-[4-methyl-2-(1-phenyl-vinyl) phenoxymethyl]-pyrrolidine-1-carboxylic acid tertiary butylester Preparation: 2.09 g (9.9 mmole) 1-hydroxy-4-methyl-2-(1-phenyl-vinyl)-benzene 2.00 g (9.9 mmole) N-Boc-(S)-prolinole 1.90 g (10.9 mmole) diethylazodicarboxylate 2.86 g (10.9 mmole) triphenylphosphine 50 ml abs. THF Method:

To a solution of 2.09 g (9.9 mmole) 1-hydroxy-4-methyl-2-(1-phenyl-vinyl)-benzene, 2.00 g (9.9 mmole) N-Boc-(S)-prolinole and 2.86 g (10.9 mmole) triphenylphosphine in 50 ml THF 1.90 g (10.9 mmole) diethylazodicarboxylate are added dropwise. The reaction mixture is heated for 20 hours with recycling. Then the solvent is removed on the rotary evaporator, the residue is absorbed in dichloromethane and the solution is filtered through aluminium oxide (basic, activity II–III). Following removal of the solvent, the raw product obtained in this way is cleaned by column chromatography on silica gel with toluene/MTBE (ratio of volumes=20/1) as the eluant. 3.13 g (7.9 mmole, 80%)2-[4-methyl-2-(1-phenyl-vinyl)-phenoxymethyl]-pyrrolidine-1-carboxylic acid tertiary butylester are obtained.

Yield: 3.13 g (7.9 mmole, 80%)2-[4-methyl-2-(1-phenyl-vinyl)-phenoxymethyl]-pyrrolidine-1-carboxyl acid tertiary butylester Spectroscopic Data: 2-[4-methyl-2-(1-phenyl-vinyl)-phenoxymethyl]-pyrrolidine-1-carboxylic acid tertiary butylester (1.5/1 diastereomer mixture)

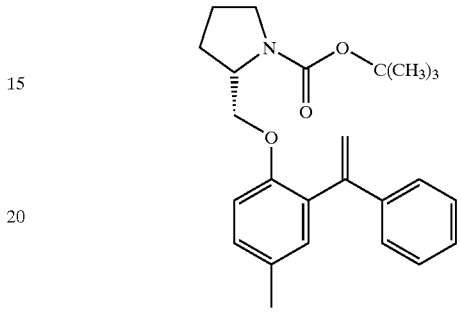

$^1$H-NMR (400 MHz, CDCl$_3$): δ [ppm]=1.26 (m, 1.4H NCH$_2$NCH$_2$), 1.43 (s, 9 H, C(CH$_3$)$_3$), 1.54 (m, 2.6 H, NCH$_2$CH$_2$, NCHCH$_2$), 2.30 and 2.31 (2×s, 3 H, CH$_3$), 3.02–3.25 (m, 2 H, NCH$_2$), 3.54 (*t, $^3$J=8.5 Hz, 0.6 H, OCH$_2$), 3.70–3.94 (m, 2.4 H, OCH$_2$, NCH), 5.27 (d, $^2$J=4.3 Hz, 1 H, =CH$_2$), 5.66 (s, 1 H, =CH$_2$), 6.87 (m, 1 H, PhH), 6.96–7.29 (m, 7 H, PhH). $^{13}$C-NMR (100 MHz, CDCl$_3$): δ [ppm]=20.4 (CH$_3$), 22.6 and 23.7 (CH$_2$), 27.3 and 28.0 (CH$_2$), 28.5 (3×C(CH$_3$)$_3$), 46.4 and 46.8 (NCH$_2$), 55.7 and 55.9 (NCH), 68.0 and 68.3 (OCH$_2$), 79.0 and 79.4 (CMe$_3$), 111.9 (CH$_{arom}$), 114.9 and 115.2 (=CH$_2$), 125.7 and 126.0 (CH$_{arom}$), 126.3 (2×CH$_{arom}$), 128.0 (2×CH$_{arom}$), 128.2 and 128.9 (CH$_{arom}$), 130.0 and 130.7 (Cq$_{arom}$), 131.8 and 132.0 (CH$_{arom}$), 137.7 (Cq$_{arom}$), 141.4 (Cq$_{arom}$), 147.5 (Cq$_{olefin}$), 154.0 (Cq$_{arom}$), 154.4 and 154.5 (NCOO$^t$Bu).

MS (EI, 70EV): m/z [%]=393 (M$^+$, 15), 337 (4), 320 (5), 293 (33), 278 (2), 226 (4), 209 (44), 195 (16), 165 (19), 128 (42), 114 (62), 70 (87), 57 (100). Specific Rotation: [α]$_D^{20}$=−45.5° (c=0.89, diethylether)

| Elementary analysis: (C$_{25}$H$_{31}$NO$_3$, M = 393.23) | | | |
|---|---|---|---|
| theor.: | C 76.3 | H 7.9 | N 3.6 |
| actual: | C 76.0 | H 8.0 | N 3.5 |

EXAMPLE 17

Production of 2-[4-methyl-2-(1-phenyl-vinyl)-phenoxymethyl]-pyrrolidine

Preparation: 1.76 g (4.5 mmole) 2-[4-methyl-2-(1-phenyl-vinyl)-phenoxymethyl]-pyrrolidine-1-carboxylic acid tertiary butylester 5.4 ml trifluoroacetic acid 22 ml abs. CH$_2$Cl$_2$ Method:

To a solution of 1.76 g (4.5 mmole)2-[4-methyl-2-(1-phenyl-vinyl)-phenoxymethyl]-pyrrolidine-1-carboxylic acid tertiary butylester in 22 ml abs. CH$_2$Cl$_2$ at 0° C. 5.4 ml trifluoroacetic acid are added and the reaction solution is agitated for 1 h at the same temperature. Then the reaction mixture is reduced on the rotary evaporator and the residue is absorbed in 20 ml dichloromethane. The solution is displaced with 20 ml concentrated ammonia solution and the organic phase is separated off. The aqueous phase is extracted twice with 10 ml dichloromethane in each case and the purified organic phases are dried through MgSO$_4$. The solvent is removed on the rotary evaporator and the raw product obtained in this way is cleaned by column chromatography on silica gel with MTBE/cyclohexane/ethanol/diisopropylamine (ratio of volumes=3/1/1+Vo.–%) as the eluant. 1.31 g (4.5 mmole, 100%)2-[4-methyl-2-(1-phenyl-vinyl)-phenoxymethyl]-pyrrolidine are obtained.

Yield: 1.31 g (4.5 mmole, 100%)2-[4-methyl-2-(1-phenyl-vinyl)-phenoxymethyl]-pyrrolidine.

Spectroscopic Data: 2-[4-methyl-2-(1-phenyl-vinyl)phenoxymethyl]-pyrrolidine.

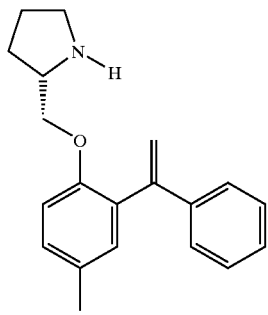

$^1$H-NMR (400 MHz, CDCl$_3$): δ [ppm]=1.18 (m, 1H NCH$_2$NCH$_2$), 1.56 (m, 3 H, NCH$_2$CH$_2$, NCHCH$_2$), 1.85 (s (b), 1 H, NH) 2.33 (s, 3 H, CH$_3$), 2.57 (m, 1 H, NCH$_2$), 2.65 (m, 1 H, NCH$_2$), 3.00 (m, 1 H, NCH), 3.64 (dd, $^2$J=8.9 Hz, $^3$J=6.3 Hz, 1 H, OCH$_2$), 3.77 (dd, $^2$J=8.9 Hz, $^3$J=4.0 Hz, 1 H, OCH$_2$), 5.30 (d, $^2$J=1.0 Hz, 1 H, =CH$_2$), 5.60 (d, $^2$J=1.0 Hz, 1 H, =CH$_2$), 6.73 (d, $^3$J=8.3 Hz, 1 H, PhH), 7.08–7.14 (m, 2 H, PhH), 7.24–7.30 (m, 5 H, PhH). $^{13}$C-NMR (100 MHz, CDCl$_3$): δ [ppm]=20.4 (CH$_3$), 24.8 (CH$_2$), 26.9 (CH$_2$), 46.2 (NCH$_2$), 57.4 (NCH), 69.7 (OCH$_2$), 111.4 (CH$_{arom}$), 115.4 (=CH$_2$), 126.2 (2×CH$_{arom}$), 127.2 (CH$_{arom}$), 128.1 (2×CH$_{arom}$), 129.4 (CH$_{arom}$), 129.8 (Cq$_{arom}$), 130.6 (Cq$_{arom}$), 131.9 (CH$_{arom}$), 141.8 (Cq$_{arom}$), 147.9 (Cq$_{olefin}$), 153.8 (Cq$_{arom}$). MS (EI, 70EV): m/z [%]= 293 (M$^+$, 15), 211 (4), 209 (4), 195 (1), 178 (3), 165 (6), 152 (2), 70 (100).

Specific Rotation:

[α]$_D^{20}$=+15.3° (c=1.00, diethylether)

| Elementary analysis: C$_{20}$H$_{23}$NO, M = 239.2) | | | |
|---|---|---|---|
| theor.: | C 81.9 | H 7.9 | N 4.8 |
| actual: | C 81.3 | H 7.9 | N 4.5 |

EXAMPLE 18

Production of diphenylphosphanyl-[4-methyl-2-(1-phenyl-vinyl)-phenoxymethyl]-pyrrolidine Preparation: 1.31 g (4.5 mmole) 2-[4methyl-2-(1-phenyl-vinyl)-phenoxymethyl]-pyrrolidine
1.00 g (4.6 mmole) P-chlorodiphenylphosphine
1.13 g (11.2 mmole) triethylamine
15 ml abs. toluene Method:

To a solution of 1.31 g (4.5 mmole)2-[4-methyl-2-(1-phenyl-vinyl)-phenoxymethyl]-pyrrolidine and 1.13 g (11.2 mmole) triethylamine in 12 ml abs. toluene at 0° within 30 minutes 1.00 g (4.6 mmole) P-chlorodiphenylphosphine in 3 ml abs. toluene are added dropwise. The reaction solution is left under agitation at RT for 20 h. Then the resultant triethylammonium chloride is filtered off, the residue is recleaned with 20 ml toluene and the filtrate is reduced on the rotary evaporator. Cleaning of the raw product obtained takes place by column chromatography on silica gel with MTBE/cyclohexane/diisopropylamine (ratio of volumes=5/1+10 Vol–%) as the eluant. 1.31 g (2.7 mmole, 61%) diphenylphosphanyl-[4-methyl-2-(1-phenyl-vinyl)-phenoxymethyl]-pyrrolidine are obtained.

Yield: 1.31 g (2.7 mmole, 61%)diphenylphosphanyl-[4-methyl-2-(1-phenyl-vinyl)-phenoxymethyl]-pyrrolidine.

Spectroscopic Data: Diphenylphosphanyl-[4-methyl-2-(1-phenyl-vinyl)-phenoxymethyl]-pyrrolidine

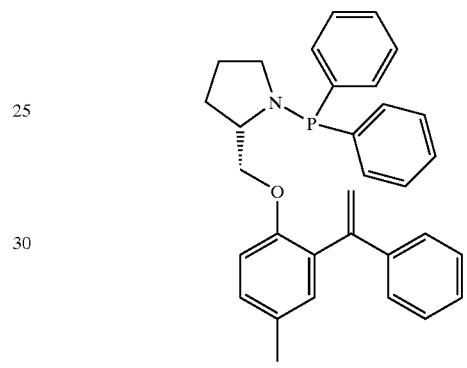

$^1$H-NMR (400 MHz, CDCl$_3$): δ [ppm]=1.26 (m, 1H NCH$_2$NCH$_2$), 1.44 (m, 3 H, NCH$_2$CH$_2$, NCHCH$_2$), 2.31 (s, 3 H, CH$_3$), 2.53 (m, 1 H, NCH$_2$), 2.80 (m, 1 H, NCH$_2$), 3.48 (m, 1 H, NCH), 3.62 (m, 1 H, OCH$_2$), 3.92 (m, 1H, OCH$_2$), 5.29 (d, $^2$J=1.5 Hz, 1 H, =CH$_2$), 5.64 (d, $^2$J=1.5 Hz, 1 H, =CH$_2$), 6.78 (d, $^3$J=8.5 Hz, 1 H, PhH), 7.07 (m, 2 H, PhH), 7.19–7.34 (m, 15 H, PhH). $^{13}$C-NMR (100 MHz, CDCl$_3$): δ [ppm]=20.4 (CH$_3$), 25.1 (NCH$_2$CH$_2$), 28.9 (NCHCH$_2$, $^3$J$_{C-P}$=5.8 Hz), 47.0 (NCH$_2$, $^2$J$_{C-P}$=8.7 Hz), 61.4 (NCH, $^2$J$_{C-P}$=29.2 Hz), 70.8 (OCH$_2$, $^3$J$_{C-P}$=5.8 Hz), 112.0 (CH$_{arom}$), 115.1 (=CH$_2$), 126.4 (3×CH$_{arom}$), 127.1 (CH$_{arom}$), 127.8 (CH$_{arom}$), 127.9 (3×CH$_{arom}$), 128.0 (2×CH$_{arom}$), 128.9 (2×CH$_{arom}$), 129.6 (Cq$_{arom}$), 130.8 (Cq$_{arom}$), 131.2 (2×CH$_{arom}$), 131.9 (CH$_{arom}$), 132.7 (2×CH$_{arom}$), 138.5 (P-Cq$_{arom}$, $^1$J$_{P-C}$=16.5 Hz), 139.5 (P-Cq$_{arom}$, $^1$J=6.8 Hz), 141.6 (Cq$_{arom}$), 147.7 (Cq$_{olefien}$), 154.1 (Cq$_{arom}$). $^{31}$P-NMR (202 MHz, CDCl$_3$): δ [ppm]= 46.2. MS (EI, 70EV): m/z [%]=477 (M$^+$, 15), 395 (37), 379 (15), 317 (1), 292 (6), 280 (5), 267 (11), 254 (54), 185 (100), 152 (10), 91 (9).

EXAMPLE 19

Hydroaminomethylation of 4-methyl-2-(1-phenyl-vinyl)-phenol

Preparation:

0.210 g (1.0 mmole) 4-methyl-2-(1-phenyl-vinyl)-phenol
0.10 ml (1.15 mmole) morpholine
6.0 mg (12 μmole) [RhCl(cod)]$_2$
10 ml abs. dioxane Method:

0.421 g (2.0 mmole) 4-methyl-2-(1-phenyl-vinyl)-phenol, 0.10 ml (1.15 mmole) morpholine, 6.0 mg (12 μmole) [RhCl(cod)]$_2$ and 10 ml abs. dioxane are agitated in a pressure vessel for 3 days at 120° C. and under a pressure of 90 bar synthesis gas (CO:H$_2$=7.2). Following cooling and relieving of the pressure vessel, the reaction solution undergoes absorptive filtering (eluant: diethylether, then ethanol) through aluminium oxide (activity II–III, basic). Following removal of the solvent, the cleaning of the raw product takes place by column chromatography on silica gel with cyclohexane/MTBE (ratio of volumes=1/1) as the eluant. 255 mg (0.82 mmole, 82%) 4-methyl-2-(3-morpholin-4-yl-1-phenyl-propyl)-phenol are obtained.

Yield: 255 mg (0.82 mmole, 82%) 4-methyl-2-(3-morpholin-4-yl-1-phenyl-propyl)-phenol.

Spectroscopic Data: 4-methyl-2-(3-morpholin-4-yl-1-phenyl-propyl)-phenol.

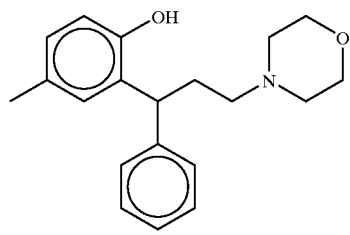

$^1$H-NMR (400 MHz, CDCl$_3$): δ [ppm]=2.09 (s, 3 H, CH$_3$), 2.31–2.49 (6 H, CH$_2$+2×NCH$_2$), 2.65 (brs, 2 H, NCH$_2$), 3.78–3.89 (4 H, 2×OCH$_2$), 4.44 (dd, $^3$J=12.8, 3.7 Hz, CHArAr'), 6.48 (s, 1H, OH), 6.85 (m, 2 H, Ar—H), 7.19–3.33 (6 H, Ar—H). $^{13}$C-NMR (100 MHz, CDCl$_3$): δ [ppm]=20.6 (CH$_3$), 30.4 (CH$_2$), 38.1 (CHArAr'), 54.5 (2×NCH$_2$), 58.3 (NCH$_2$), 66.3 (2×OCH$_2$), 117.4 (CH$_{arom}$) 126.2 (CH$_{arom}$), 128.0 (2×CH$_{arom}$), 128.3 (2×CH$_{arom}$), 129.2 (2×CH$_{arom}$), 129.5 (Cq$_{arom}$), 130.7 (Cq$_{arom}$), 144.5 (Cq$_{arom}$), 153.4 (Cq$_{arom}$).

Synthesis of Rac-tolterodine

Preparation:

0.210 g (1.0 mmole) 4-methyl-2-(1-phenyl-vinyl)-phenol 0.17 ml (1.2 mmole) diisopropylamine 6.0 mg (12 μmole) [RhCl(cod)]$_2$ 10 ml abs. dioxane Method:

0.210 g (1.0 mmole) 4-methyl-2-(1-phenyl-vinyl)-phenol, 0.17 ml (1.2 mmole) diisopropylamine, 6.0 mg (12 μmole) [RhCl(cod)]$_2$ and 10 ml abs. dioxane are agitated in a pressure vessel for 3 days at 120° C. and under a pressure of 90 bar synthesis gas (CO:H$_2$=7.2). Following cooling and relieving of the pressure vessel, the reaction solution undergoes absorptive filtering (eluant: diethylether, then ethanol) through aluminium oxide (activity II–III, basic). The solvents are distilled off. 295 mg of a raw product are obtained that, according to NMR, contains 71% 2-(3-diisopropylamino-1-phenyl-propyl)-4-methyl-phenol and 29% 6-methyl-4-phenyl-chroman-2-ol.

Yield: 228 mg (0.70 mmole, 70%) 2-(3-diisopropylamino-1-phenyl-propyl)-4-methyl-phenol Spectroscopic Data:

2-(3-diisopropylamino-1-phenyl-propyl)-4-methyl-phenol

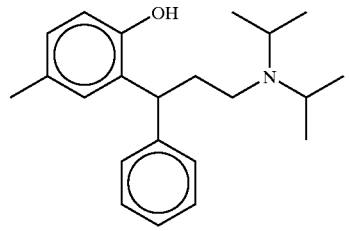

The spectroscopic data correspond to those of the literature P. G. Andersson, H. E. Schenk, K. Österlund *J. Org. Chem.* 1998, 63, 8067.

What is claimed is:

1. A method for producing 3,3-diarylpropylamines of the general formula (I)

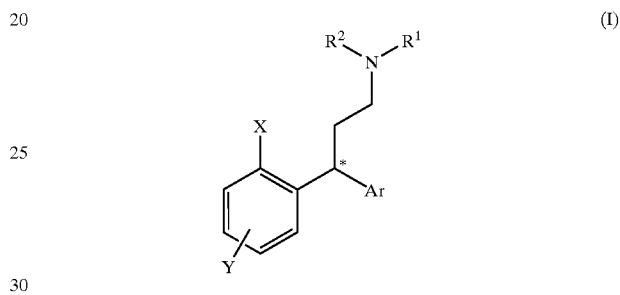

wherein

Ar represents a substituted or unsubstituted aryl radical,

X represents H, OH or OR$^3$,

Y represents Cl, Br, I, CN, CHO, CH$_2$OR, COOH, COOR, wherein R represents C$_1$–C$_{10}$-alkyl or a substituted or unsubstituted aryl radical, or C$_1$–C$_{10}$-alkyl, R$^1$, R$^2$ represents C$_1$–C$_{10}$-alkyl or C$_3$–C$_8$-cycloalkyl, wherein R$^1$ and R$^2$ can be linked to form a cyclical structure, and wherein R$^3$ represents a radical derived from one of the following compounds:

(i) the amino acids D-proline, L-proline, D-alanine, L-alanine, D-asparagine, L-asparagine, D-asparagine acid, L-asparagine acid, D-glutamine, L-glutamine, D-glutamine acid, L-glutamine acid, D-phenylalanine, L-phenylalanine, D-histidine, L-histidine, D-leucine, L-leucine, D-serine, L-serine, L-threonine, D-threonine, D-tryptophane, L-tryptophane, D-tyrosine, L-tyrosine, D-valine, L-valine, D-cysteine, L-cysteine, D-methionine, L-methionine, D-isoleucine, L-isoleucine, or alcohols that are produced by these amino acids by reduction of the carboxylic acid function to the hydroxymethylene unit, (ii) the amino acids N-diphenylphosphanyl-D-alanine, N-diphenylphosphanyl-L-alanine, N-diphenylphosphanyl-D-proline, N-diphenylphosphanyl-L-proline, N-diphenylphosphanyl-D-phenylalanine, N-diphenylphosphanyl-L-phenylalanine, and the alcohols that are produced by these amino acids by reduction of the carboxylic acid function to the hydroxymethylene unit, (iii) α-hydroxycarboxylic acid derivatives having the general formula

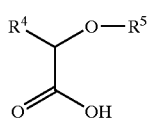

respectively in the form of both optical antipodes, wherein $R^4$ represents a linear or branched $C_1$–$C_{10}$-alkyl group or cycloalkyl group or a substituted or unsubstituted aryl radical and $R^5$ represents $C_1$–$C_{10}$-alkyl, cycloalkyl, acyl, alkoxycarbonyl, benzoyl, diphenylphosphanyl, dicyclohexylphosphanyl or diarylphosphanyl, (iv) compounds having the general formula

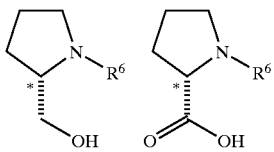

wherein $R^6$ represents a substituent selected from the group consisting of $PPh_2$, $P(C_6H_{11})_2$, $P(aryl)_2$, alkyl, acyl, alkoxycarbonyl, benzoyl, arylcarbonyl, diarylphosphanyl and dicyclohexylphosphanyl, and their stereoisomers, (v) compounds having the general formula

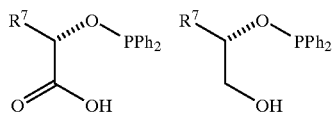

wherein $R^7$ represents a linear or branched $C_1$–$C_{10}$-alkyl group or a substituted or unsubstituted aryl radical, and stereoisomers thereof, (vi) the acids
- (R)-acetoxyphenylacetic acid,
- (R)- and (S)-1,4-benzodioxane-2-carboxylic acid,
- (R)-(−)- and (S)-(+)-hexahydro-acetoxymandelic acid,
- (2R,3S)-2,3-O-isopropylidene-2,3-dihydroxybutyric acid and its stereoisomers,
- (+)- and (−)-menthyloxyacetic acid,
- (R)- and (S)-3-phenyl-2-acyloxypropionic acid,
- (R)- and (S)-acetoxymandelic acids,
- (R)- and (S)-α-methoxy-α-trifluoromethylphenylacetic acid,
- (S)-(+)-alpha-methoxyphenylacetic acid,
- (R)- and (S)-5-oxo-tetrahydrofurane-2-carboxylic acid, and the alcohols that are produced from these acids by reduction of the carboxylic acid function to the hydroxymethylene unit, (vii) compounds having the general formula

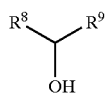

wherein $R^8$ represents a substituted or unsubstituted aryl radical and $R^9$ hydrogen or a linear or branched $C_1$–$C_{10}$-alkyl radical, (viii) α-naphthol, β-naphthol or (R)- or (S)-1-(9-anthryl)-2,2,2-trifluoroethanol, (ix) 2-methylamino-1-phenyl-propan-1-ol (ephedrine) in all stereomer forms, or $R^3$ represents one or the following radicals:

(x) phosphite radicals with the general formula $—P(OR^{10})(OR^{11})$, wherein $R^{10}$ and $R^{11}$ are aryl groups which can be the same or different or $R^{10}$ and $R^{11}$ taken in combination from a polycyclic aryl or biaryl diradical, (xi) $C_1$–$C_{10}$-alkyl, branched or linear, (xii) acyl, (xiii) benzyl or substituted benzyl radicals, characterised in that compounds with the general formula (II)

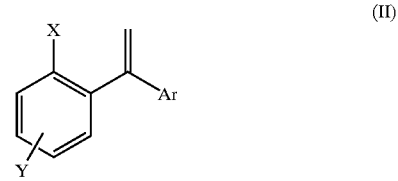

wherein X, Y and Ar as defined above, are transformed together with carbon monoxide (CO) and hydrogen ($H_2$) in the presence of a transition metal catalyst and the resultant oxo compounds are allowed to react in the presence of a transition metal catalyst with an amine of the general formula $HNR^1R^2$, wherein $R^1$ and $R^2$ are as defined above.

2. A method for producing 3,3-diarylpropylamines of the general formula (III)

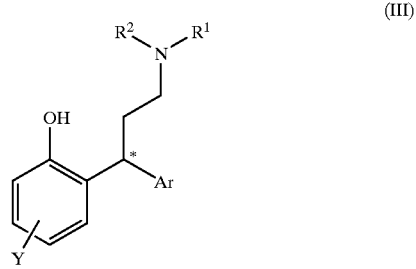

wherein Ar represents a substituted or unsubstituted aryl radical,

Y represents Cl, Br, I, CN, CHO, $CH_2OR$, COOH, COOR, wherein R represent $C_1$–$C_{10}$-alkyl or a substituted or unsubstituted aryl radical, or $C_1$–$C_{10}$-alkyl, $R^1$, $R^2$ represents $C_1$–$C_{10}$-alkyl or $C_3$–$C_8$-cycloalkyl, wherein $R^1$ and $R^2$ can be linked to form a cyclical structure, characterised in that compounds of the general formula (IV)

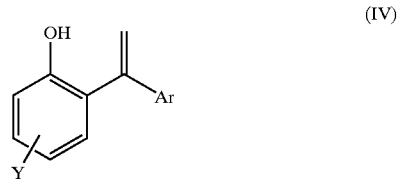

wherein Y and Ar are defined as above, are transformed with carbon monoxide (CO) and hydrogen ($H_2$) in the presence of a transition metal catalyst to a chromium/lactol system

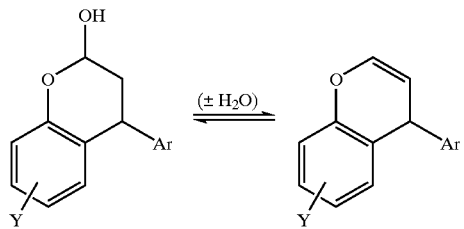

wherein Y and Ar are as defined above, and the transformation product, in the presence of a transition metal catalyst, is allowed to react with an amine of the general formula $HNR^1R^2$, wherein $R^1$ and $R^2$ are as defined above.

3. A method according to claim 1 or 2, wherein the reaction is conducted at a temperature of between 50 and 200° C.

4. A method according to claim 1 or 2, wherein the reaction is conducted at a temperature of between 100 and 140° C.

5. A method according to claim 1 or 2, wherein the reaction is conducted at a pressure of between 40 and 200 bar.

6. A method according to claim 1 or 2, wherein the reaction is conducted at a pressure of between 80 and 120 bar.

7. A method according to claim 6, wherein the $CO/H_2$ pressure ratio is between 10/90 and 90/10.

8. A method according to claim 6, wherein the $CO/H_2$ pressure ratio is between 70/30 and 90/10.

9. A method according to claim 1 or 2, wherein the reaction is conducted over a period of between 2 hours and 4 days.

10. A method according to claim 1 or 2, wherein the reaction is conducted over a period of between 1 and 3 days.

11. A method according to claim 1 or 2, wherein the catalyst contains rhodium.

12. A method according to claim 1 or 2, wherein the catalyst contains rhodium and is formed in-situ from a catalyst precursor and a ligand.

13. A method according to claim 12, wherein the catalyst precursor is selected from the group consisting of [Rh(cod)Cl]$_2$ and Rh(acac)(CO)$_2$.

14. A method according to claim 12, wherein the ligand is a compound selected from the group consisting of:
(2-(diphenylphosphino)-1,1'-binaphthalen-2'-yl-(S)-1,1'-binaphthalene-2,2'-diylphosphite (BINAPHOS),
(2,2-dimethyl-4,5-diphenylphosphinomethyl)-1,3-dioxolane, (DIOP),
(2,2-dimethyl-4,5-bis(5H-dibenzophosphol-5-ylmethyl)-1,3-dioxolane,
1,4-bis(diphenylphosphino)butane,
2,3-bis(diphenylphosphino)butane,
1,2-bis(diphenylphosphinomethyl)cyclobutane,
1,2-bis(5H-dibenzophosphol-5-ylmethyl)cyclobutane,
1,2-bis(diphenylphosphinomethyl)cyclohexane,
1,2-bis(5H-dibenzophosphol-5-ylmethyl)cyclohexane,
(2S,4S)-N-tert.-butoxycarbonyl-4-diphenylphosphino-2-diphenylphosphinomethyl-pyrrolidine (BPPM),
1,2-bis(diphenylphosphinoxy)cyclohexane,
Benzyl-methyl-phenylphosphine,
Cyclohexyl-o-anisyl-methylphosphine,
Neomenthyldiphenylphosphine,
Phenyl-o-anisyl-methylphosphine,
ortho-diphenylphosphanylbenzoyl,
tributylphosphine,
2,2'-bis(diphenylphosphino)-1,1'-binaphthyl (BINAP) and mixtures or stereoisomers of said compounds.

15. A method according to claim 12, wherein the ligand is selected from the group consisting of tributylphosphine, (+)- and (−)-(2,2-dimethyl-4,5-diphenylphosphinomethyl)-1,3-dioxolane, (R)- and (S)-BINAP, and (R,S)-BINAPHOS and their stereoisomers.

16. A method according to claim 15, wherein the ligand is tributylphosphine and the molar ratio of tributylphosphine to rhodium is between 1:1 and 25:1.

17. A method according to claim 15, wherein the ligand is tributylphosphine and the molar ratio of tributylphosphine to rhodium is between 4:1 and 10:1.

18. A method according to claim 15, wherein the ligand is selected from the group consisting of (R)- and (S)-BINAP, and the molar ratio of BINAP to rhodium is between 1:1 and 6:1.

19. A method according to claim 15, wherein the ligand is selected from the group consisting of (R)- and (S)-BINAP, and the molar ratio of BINAP to rhodium is between 1:1 and 2:1.

20. A method according to claim 15, wherein the ligand is selected from the group consisting or (R,S)-BINAPHOS and its stereoisomers, and the molar ratio of BINAPHOS to rhodium is between 1:1 and 6:1.

21. A method according to claim 15, wherein the ligand is selected from the group consisting of (R,S)-BINAPHOS and its stereoisomers, and the molar ratio of BINAPHOS to rhodium is between 1:1 and 2:1.

* * * * *